United States Patent
Fossel

(10) Patent No.: US 9,289,495 B2
(45) Date of Patent: Mar. 22, 2016

(54) SYSTEMS AND METHODS FOR TREATMENT OF ALLERGIES AND OTHER INDICATIONS

(75) Inventor: Eric T. Fossel, Cambridge, MA (US)

(73) Assignee: Strategic Science & Technologies, LLC, Cambridge, MA (US)

( * ) Notice: Subject to any disclaimer, the term of this patent is extended or adjusted under 35 U.S.C. 154(b) by 59 days.

(21) Appl. No.: 13/977,511

(22) PCT Filed: Dec. 29, 2011

(86) PCT No.: PCT/US2011/067987
§ 371 (c)(1),
(2), (4) Date: Oct. 23, 2013

(87) PCT Pub. No.: WO2012/092523
PCT Pub. Date: Jul. 5, 2012

(65) Prior Publication Data
US 2014/0044774 A1    Feb. 13, 2014

Related U.S. Application Data

(60) Provisional application No. 61/428,003, filed on Dec. 29, 2011, provisional application No. 61/428,213, filed on Dec. 29, 2011.

(51) Int. Cl.
| | | |
|---|---|---|
| A61K 31/74 | (2006.01) | |
| A61K 47/02 | (2006.01) | |
| A61K 45/06 | (2006.01) | |
| A61K 9/00 | (2006.01) | |
| A61K 47/10 | (2006.01) | |
| A61K 47/18 | (2006.01) | |
| A61K 47/26 | (2006.01) | |
| A61K 47/36 | (2006.01) | |

(52) U.S. Cl.
CPC ............. *A61K 47/02* (2013.01); *A61K 9/0014* (2013.01); *A61K 31/74* (2013.01); *A61K 45/06* (2013.01); *A61K 47/10* (2013.01); *A61K 47/183* (2013.01); *A61K 47/26* (2013.01); *A61K 47/36* (2013.01)

(58) Field of Classification Search
CPC . A61K 2300/00; A61K 31/198; A61K 9/014; A61K 9/06; A61K 31/506; A61K 47/10; A61K 31/519; A61K 31/522; A61K 47/02; A61K 31/192; A61K 47/36; A61K 47/183; A61K 9/107; A61K 47/26; A61K 9/7023; A61K 8/44; A61K 31/403; A61K 31/404; A61K 31/4045; A61K 31/4196; A61K 31/422
See application file for complete search history.

(56) References Cited

U.S. PATENT DOCUMENTS

| | | |
|---|---|---|
| 3,574,854 A | 4/1971 | Bossard |
| 3,960,782 A | 6/1976 | Daley et al. |
| 4,185,100 A | 1/1980 | Rovee et al. |
| 4,681,897 A | 7/1987 | Brand |
| 4,692,462 A | 9/1987 | Banerjee |
| 4,702,913 A | 10/1987 | Marty |
| 4,722,837 A | 2/1988 | Cameron |
| 4,732,892 A | 3/1988 | Sarpotdar et al. |
| 4,743,442 A | 5/1988 | Raaf et al. |
| 4,871,839 A | 10/1989 | Gibson |
| 4,940,456 A | 7/1990 | Sibalis et al. |
| 4,945,901 A | 8/1990 | Burcke, Jr. |
| 4,950,654 A | 8/1990 | Horn et al. |
| 4,976,952 A | 12/1990 | Lang et al. |
| 5,008,248 A | 4/1991 | Bywater et al. |
| 5,028,435 A | 7/1991 | Katz et al. |
| 5,158,761 A | 10/1992 | Kamishita et al. |
| 5,180,743 A | 1/1993 | Watanabe et al. |
| 5,210,099 A | 5/1993 | Mody et al. |
| 5,215,759 A | 6/1993 | Mausner |
| 5,217,652 A | 6/1993 | Iovanni |
| 5,217,997 A | 6/1993 | Levere et al. |
| 5,254,331 A | 10/1993 | Mausner |
| 5,256,678 A | 10/1993 | Nakaguchi |
| 5,332,758 A | 7/1994 | Nakata et al. |
| 5,391,550 A | 2/1995 | Carniglia et al. |

FOREIGN PATENT DOCUMENTS

| | | |
|---|---|---|
| CA | 2337772 | 1/2000 |
| CA | 2415392 A1 | 1/2002 |

(Continued)

OTHER PUBLICATIONS

[No Author Listed] "Xanthan gum used in cosmetic products." Dermaxime: bio-cellular skin products. Available at http://www.dermaxime.com/xanthan.htm. Last accessed Apr. 23, 2009. 4 pages.
[No Author Listed] "Xanthan gum." Wikipedia. Available at http://en.wikipedia.org/wiki/Xanthan. Last accessed Apr. 13, 2009. 3 pages.
[No Author Listed] BioSpace Press Release Transdermal Ibuprofen development Complete: NDA to Be Filed (web page) http://biospace.com/news_story.aspx?NewsEntityId=18470820. Published Dec. 16, 2004. 2 pages.
[No Author Listed] MoonDragon's Health & Wellness: Nutrition Basics: Amino Acids-Arginine. Unknown date. 10 pages.
[No Author Listed] Peripheral Vascular Disease—Wikipedia (web page) http://en.wikipedia.org/wiki/Peripheral_vascular_disease [Jan. 18, 2010]. 5 pages.
[No Author Listed] Peripheral Vascular Disease (web page) http://www.americanheart.org/presenter.jhtml?identifier=4692 [Jan. 18, 2010]. 2 pages.
[No Author Listed] Sex and Sexuality Orgasm Information. Extended Orgasm. Unknown date. 7 pages.
Argiolas, Nitric Oxide is a Central Mediator of Penile Erection. Neuropharmacology, vol. 33, No. 11, pp. 1339-1344 (1994).

(Continued)

*Primary Examiner* — Lezah Roberts
*Assistant Examiner* — Nannette Holloman
(74) *Attorney, Agent, or Firm* — Wolf, Greenfield & Sacks, P.C.

(57) ABSTRACT

The present invention generally relates to the transdermal delivery of various compounds. In some aspects, transdermal delivery may be facilitated by the use of a hostile biophysical environment. One set of embodiments provides a composition for topical delivery comprising an $H_1$ antihistamine and/or a salt thereof, and optionally, a hostile biophysical environment and/or a nitric oxide donor. In some cases, the composition may be stabilized using a combination of a stabilization polymer (such as xanthan gum, KELTROL® BT and/or KELTROL® RD), propylene glycol, and a polysorbate surfactant such as Polysorbate 20, which combination unexpectedly provides temperature stability to the composition, e.g., at elevated temperatures such as at least 40° C. (at least about 104° F.), as compared to compositions lacking one or more of these.

45 Claims, No Drawings

(56) References Cited

U.S. PATENT DOCUMENTS

| | | |
|---|---|---|
| 5,405,919 A | 4/1995 | Keefer et al. |
| 5,428,070 A | 6/1995 | Cooke et al. |
| 5,439,938 A | 8/1995 | Snyder et al. |
| 5,464,954 A | 11/1995 | Kimura et al. |
| 5,476,852 A | 12/1995 | Cauwenbergh |
| 5,498,420 A | 3/1996 | Edgar et al. |
| 5,505,958 A | 4/1996 | Bello et al. |
| 5,527,797 A | 6/1996 | Eisenberg et al. |
| 5,538,740 A | 7/1996 | Abad |
| 5,543,430 A | 8/1996 | Kaesemeyer |
| 5,573,776 A | 11/1996 | Harrison et al. |
| 5,575,994 A | 11/1996 | Fontanelli |
| 5,576,351 A | 11/1996 | Yoshimura et al. |
| 5,595,753 A | 1/1997 | Hechtman |
| 5,605,685 A | 2/1997 | Tseng et al. |
| 5,629,002 A | 5/1997 | Weuffen et al. |
| 5,632,981 A | 5/1997 | Saavedra et al. |
| 5,643,586 A | 7/1997 | Perricone |
| 5,645,859 A | 7/1997 | Chaudhuri et al. |
| 5,648,101 A | 7/1997 | Tawashi |
| 5,656,264 A | 8/1997 | Hanada et al. |
| 5,691,423 A | 11/1997 | Smith et al. |
| 5,698,738 A | 12/1997 | Garfield et al. |
| 5,714,472 A | 2/1998 | Gray et al. |
| 5,762,963 A | 6/1998 | Byas-Smith |
| 5,789,442 A | 8/1998 | Garfield et al. |
| 5,807,957 A | 9/1998 | Samour et al. |
| 5,824,658 A | 10/1998 | Falk et al. |
| 5,853,768 A | 12/1998 | Altadonna |
| 5,891,459 A | 4/1999 | Cooke et al. |
| 5,891,472 A | 4/1999 | Russell |
| 5,895,658 A | 4/1999 | Fossel |
| 5,906,822 A | 5/1999 | Samour et al. |
| 5,911,980 A | 6/1999 | Samour et al. |
| 5,922,332 A | 7/1999 | Fossel |
| 5,925,372 A | 7/1999 | Berner et al. |
| 5,939,094 A | 8/1999 | Durif et al. |
| 5,976,566 A | 11/1999 | Samour et al. |
| 5,985,317 A | 11/1999 | Venkateshwaran et al. |
| 6,036,977 A | 3/2000 | Drizen et al. |
| 6,103,275 A | 8/2000 | Seitz et al. |
| 6,117,872 A | 9/2000 | Maxwell et al. |
| 6,207,713 B1 | 3/2001 | Fossel |
| 6,242,229 B1 | 6/2001 | Pineau et al. |
| 6,264,979 B1 | 7/2001 | Svedman |
| 6,287,601 B1 | 9/2001 | Russell |
| 6,312,720 B1 | 11/2001 | Katinger et al. |
| 6,375,672 B1 | 4/2002 | Aksan et al. |
| 6,387,081 B1 | 5/2002 | Cooper |
| 6,444,234 B1 | 9/2002 | Kirby et al. |
| 6,448,267 B1 | 9/2002 | Anggard et al. |
| 6,451,337 B1 | 9/2002 | Smith et al. |
| 6,458,841 B2 | 10/2002 | Fossel |
| 6,468,557 B1 | 10/2002 | Lezdey et al. |
| 6,511,991 B2 | 1/2003 | Hrabie et al. |
| 6,538,033 B2 | 3/2003 | Bing |
| 6,558,695 B2 | 5/2003 | Luo et al. |
| 6,562,370 B2 | 5/2003 | Luo et al. |
| 6,565,879 B1 | 5/2003 | Luo et al. |
| 6,582,724 B2 | 6/2003 | Hsu et al. |
| 6,586,000 B2 | 7/2003 | Luo et al. |
| 6,602,912 B2 | 8/2003 | Hsu et al. |
| 6,617,337 B1 | 9/2003 | Wilcox |
| 6,642,260 B2 | 11/2003 | Haj-Yehia |
| 6,646,006 B2 | 11/2003 | Cooke et al. |
| 6,676,962 B1 | 1/2004 | Muller |
| 6,716,436 B1 | 4/2004 | Seguin |
| 6,719,997 B2 | 4/2004 | Hsu et al. |
| 6,747,063 B2 | 6/2004 | Adams et al. |
| 6,787,152 B2 | 9/2004 | Kirby et al. |
| 6,835,392 B2 | 12/2004 | Hsu et al. |
| 6,852,739 B1 | 2/2005 | Garvey et al. |
| 6,858,232 B2 | 2/2005 | Verbiscar |
| 7,241,456 B2 | 7/2007 | Vromen |
| 7,267,829 B2 | 9/2007 | Kirby et al. |
| 7,442,690 B2 | 10/2008 | Prejean et al. |
| 7,629,384 B2 | 12/2009 | Fossel |
| 7,914,814 B2 | 3/2011 | Fossel |
| 8,603,519 B2 | 12/2013 | Fossel |
| 8,604,081 B2 | 12/2013 | Fossel |
| 9,050,365 B2 | 6/2015 | Fossel |
| 9,072,659 B2 | 7/2015 | Fossel |
| 2002/0015713 A1 | 2/2002 | Murdock et al. |
| 2002/0037854 A1 | 3/2002 | Breton et al. |
| 2002/0041903 A1 | 4/2002 | Fossel |
| 2002/0168325 A1 | 11/2002 | Lerner et al. |
| 2002/0168424 A1 | 11/2002 | Shahinpoor et al. |
| 2003/0018076 A1 | 1/2003 | Fossel |
| 2003/0028169 A1 | 2/2003 | Fossel |
| 2003/0044439 A1 | 3/2003 | Dobson et al. |
| 2003/0069618 A1 | 4/2003 | Smith et al. |
| 2003/0157185 A1 | 8/2003 | Paradise |
| 2003/0203915 A1 | 10/2003 | Fang et al. |
| 2004/0082659 A1 | 4/2004 | Cooke et al. |
| 2004/0228908 A1 | 11/2004 | Liu et al. |
| 2005/0069590 A1 | 3/2005 | Buehler et al. |
| 2005/0196418 A1 | 9/2005 | Yu et al. |
| 2007/0065463 A1 | 3/2007 | Aung-Din et al. |
| 2007/0072847 A1 | 3/2007 | Mueller et al. |
| 2007/0087977 A1 | 4/2007 | Robbins |
| 2007/0105763 A1 | 5/2007 | Ghosh |
| 2007/0253911 A1 | 11/2007 | Tamarkin et al. |
| 2008/0045909 A1 | 2/2008 | Fossel |
| 2008/0233183 A1 | 9/2008 | McCook et al. |
| 2008/0280984 A1 | 11/2008 | Fossel |
| 2008/0292684 A1 | 11/2008 | Colombo et al. |
| 2009/0105336 A1 | 4/2009 | Fossel |
| 2009/0123528 A1 | 5/2009 | Fossel |
| 2009/0142390 A1 | 6/2009 | Jackson et al. |
| 2009/0221536 A1 | 9/2009 | Fossel |
| 2009/0247635 A1 | 10/2009 | Ehrenpreis |
| 2010/0196332 A1 | 8/2010 | Wichterle et al. |
| 2010/0196517 A1 | 8/2010 | Fossel |
| 2010/0280122 A1 | 11/2010 | Fossel |
| 2010/0291195 A1 | 11/2010 | Fossel |
| 2010/0291236 A1 | 11/2010 | Sadler et al. |
| 2010/0316749 A1 | 12/2010 | Fossel |
| 2010/0317737 A1 | 12/2010 | Fossel |
| 2011/0028548 A1 | 2/2011 | Fossel |
| 2011/0182977 A1 | 7/2011 | Fossel |
| 2012/0027876 A1* | 2/2012 | Ford .......................... 424/690 |
| 2012/0108664 A1 | 5/2012 | Fossel |
| 2012/0148665 A1 | 6/2012 | Fossel |
| 2012/0258865 A1 | 10/2012 | Short et al. |
| 2013/0072498 A1 | 3/2013 | Fossel |
| 2013/0289059 A1 | 10/2013 | Fossel |
| 2014/0004176 A1 | 1/2014 | Fossel |
| 2014/0004177 A1 | 1/2014 | Fossel |
| 2014/0010866 A1 | 1/2014 | Fossel |
| 2014/0038205 A1 | 2/2014 | Raynard |
| 2014/0051707 A1 | 2/2014 | Fossel |
| 2014/0051717 A1 | 2/2014 | Fossel |
| 2014/0056971 A1 | 2/2014 | Fossel |
| 2014/0066452 A1 | 3/2014 | Fossel |
| 2014/0066511 A1 | 3/2014 | Fossel |
| 2014/0072618 A1 | 3/2014 | Fossel |
| 2014/0073697 A1 | 3/2014 | Fossel |
| 2014/0086980 A1 | 3/2014 | Fossel |
| 2015/0010619 A1 | 1/2015 | Fossel |
| 2015/0011570 A1 | 1/2015 | Fossel |
| 2015/0080470 A1 | 3/2015 | Fossel |

FOREIGN PATENT DOCUMENTS

| | | |
|---|---|---|
| CN | 101340916 A | 1/2009 |
| DE | 10128910 A1 | 12/2002 |
| EP | 0338291 A1 | 10/1989 |
| EP | 0391342 A1 | 10/1990 |
| EP | 0 399 765 A2 | 11/1990 |
| EP | 0 424 028 A2 | 4/1991 |
| EP | 1210933 A1 | 6/2002 |
| FR | 1553063 | 11/1967 |
| FR | 5940 | 4/1968 |
| FR | 2602678 | 2/1988 |

(56) References Cited

FOREIGN PATENT DOCUMENTS

| | | |
|---|---|---|
| FR | 2740453 | 4/1997 |
| FR | 2810540 | 12/2001 |
| GB | 2094142 A1 | 9/1982 |
| GB | 2126868 A | 4/1984 |
| JP | 57-053404 A | 3/1982 |
| JP | 60-252412 A | 12/1985 |
| JP | 03-093707 | 4/1991 |
| JP | 04-005231 | 9/1992 |
| JP | 05-279250 A | 10/1993 |
| JP | 6-247832 | 9/1994 |
| JP | 6-287135 A | 10/1994 |
| JP | 7-53336 | 2/1995 |
| JP | 07-316075 A | 12/1995 |
| JP | 09-143098 A | 6/1997 |
| JP | 9-208460 A | 8/1997 |
| JP | 9-241156 A | 9/1997 |
| JP | 10-167953 | 6/1998 |
| JP | 2000-186028 A | 7/2000 |
| JP | 2001-288068 A | 10/2001 |
| JP | 2002-003373 A | 1/2002 |
| JP | 2003-286129 A | 10/2003 |
| JP | 2004-059439 A | 2/2004 |
| JP | 2005-200370 A | 7/2005 |
| JP | 2007-532696 A | 11/2007 |
| RU | 2212232 C2 | 9/2003 |
| RU | 2229286 C2 | 5/2004 |
| WO | WO 88/06034 A1 | 8/1988 |
| WO | WO 92/08705 | 5/1992 |
| WO | WO 92/15276 A2 | 9/1992 |
| WO | WO 94/09750 A1 | 5/1994 |
| WO | WO 95/13060 | 5/1995 |
| WO | WO 95/15147 | 6/1995 |
| WO | WO 95/15147 A1 | 6/1995 |
| WO | WO 96/08966 A1 | 9/1995 |
| WO | WO 96/14748 | 5/1996 |
| WO | WO 96/29988 A1 | 10/1996 |
| WO | WO 97/10830 A1 | 3/1997 |
| WO | WO 97/16983 | 5/1997 |
| WO | WO 97/39760 A1 | 10/1997 |
| WO | WO 99/13717 A1 | 3/1999 |
| WO | WO 00/03689 A2 | 1/2000 |
| WO | WO 00/40215 A1 | 7/2000 |
| WO | WO 00/54773 A1 | 9/2000 |
| WO | WO 00/69469 A1 | 11/2000 |
| WO | WO 01/45713 A1 | 6/2001 |
| WO | WO 03/049593 A2 | 6/2003 |
| WO | WO 03/072039 A2 | 9/2003 |
| WO | WO 03/078437 A1 | 9/2003 |
| WO | WO 03/080104 A2 | 10/2003 |
| WO | WO 2005/081964 A2 | 9/2005 |
| WO | WO 2005/102282 A1 | 11/2005 |
| WO | WO 2005/102307 A2 | 11/2005 |
| WO | WO 2006/096360 A1 | 9/2006 |
| WO | WO 2008/076287 A2 | 6/2008 |
| WO | WO 2010/045415 A2 | 4/2010 |
| WO | WO 2010/151240 A1 | 12/2010 |

OTHER PUBLICATIONS

Bessatsu, Igaku no Ayumi, Shinkei Shikkan (A Separate Volume: Progress in Medicine, Neurological Desiases), 1999:314-6. Chinese.
Biagini et al., [Intermittent claudication: topical treatment with isosorbide dinitrate ointment. Preliminary results]. G Ital Cardiol. 1981;11(7):514-521.
Birder et al., Adrenergic and capasaicin evoked nitric oxide release from urothelium and afferent nerves in urinary bladder. American Journal of Physiology, vol. 275, pp. F226-F229 (1998). [Abstract only].
Boger et al., Restoring vascular nitric oxide formation by L-arginine improves the symptoms of intermittent claudication in patients with peripheral arterial occlusive disease. J Am Coll Cardiol. Nov. 1998;32(5):1336-44.
Bunker, C.B., et al., "Alterations in scalp blood flow after the epicutaneous application of 3% minoxidil and 0.1% hexyl nicotinate in alopecia," Correspondence, pp. 668-669 (1986).
Cooper, et al., "Transdermal Delivery of Drugs," CRC Press, vol. II, pp. 57-62 (1987).
De Boer, E.M., et al., "Does Topical Minoxidil Increase Skin Blood Flow?", Acta Derm Venereol, vol. 68, pp. 271-274 (1988).
Dietz, et al., "Is nitric oxide involved in cutaneous vasodilation during body heating in humans?" J. Appl. Physiol, vol. 76, No. 5, pp. 2047-2053 (1994).
Extended Europrean Search Report for EP 09014985.7 mailed Apr. 22, 2010.
Extended European Search Report for EP 11182318.3 mailed Jan. 20, 2012.
Extended European Search Report for EP 13167916.9 mailed Jul 30, 2013.
Extended European Search Report for EP 11173316.8 mailed Sep. 22, 2011.
Extended European Search Report for EP 11174380.3 mailed Jan. 13, 2012.
Extended European Search Report for EP 11174375.3 mailed Jan. 13, 2012.
Flick, Cosmetics Additives: An Industrial Guide. Noyes Publications, Park Ridge, New Jersey, U.S.A. 1991: 790. (The year of publication is sufficiently earlier than the effective U.S. filing date and any foreign priority date so that the particular month of publication is not in issue. See MPEP 609.04(a)).
Fossel, Improvement of Temperature and Flow in Feet of Subjects with Diabetes With Use of a Transdermal Preparation of L-Arginine. Diabetes Care, vol. 27, No. 1, Jan. 2004, pp. 284-285.
Garban et al., Effect of aging on nitric oxide-mediated penile erection in rats. Am. J. Physiol., H467-H475 (1995).
Goldenberg, The Care of the Diabetic Foot. Judy Dan Research & Treatment Centre. Available at http://www.ontariowoundcare.com/footcarephysician.htm. Last accessed Sep. 20, 2010. 9 pages.
Gutman et al., Molecular discovery of transdermal delivery nanotechnology from computer experiments and experimental R & D. Strategic Science Technologies. Presented at the Langer USA-Japan Drug Delivery Conference. Maui, Hawaii. Dec. 2011. 21 pgs.
Haldiya et al., Dermal Ulcers and Hypertension in Salt Workers. Current Science, vol. 87, No. 8, Oct. 25, 2004, pp. 1139-1141.
Hirsch et al., Peripheral Arterial Disease Detection, Awareness, and Treatment in Primary Care. J Am Med Assoc. 2001;286(11):1317-1324.
Hirvonen et al. Effect of diffusion potential, osmosis and ion-exchange on transdermal drug delivery: theory and experiments. Jornal of Controlled Release 56 (1998) 33-39.
Hwang et al., Evaluation of Vasculogenic Impotence Using Dynamic Penile Washout Test. J. Formosan Med. Assoc., vol. 89, No. 11, pp. 992-996 (1990).
International Preliminary Examination Report for PCT/US98/19429 mailed Apr. 6, 2000.
International Search Report for International Application No. PCT/US98/19429, mailed Jan. 11, 1999.
International Preliminary Report on Patentability for PCT/US2005/005726 mailed Sep. 8, 2006.
International Search Report and Written Opinion for PCT/US05/05726 mailed Sep. 19, 2005.
International Preliminary Report on Patentability for PCT/US2005/013228 mailed Nov. 2, 2006.
International Search Report and Written Opinion for PCT/US05/13228 mailed Jul. 15, 2005.
International Preliminary Report on Patentability for PCT/US2005/013230 mailed Nov. 2, 2006.
International Search Report and Written Opinion for PCT/US05/13230 mailed Oct. 28, 2005.
International Preliminary Report on Patentability for PCT/US2009/003750 mailed Jan. 12, 2012.
International Search Report and Written Opinion for PCT/US2009/003750 mailed May 19, 2010.
International Preliminary Report on Patentability for PCT/US2009/003749 mailed Jan. 12, 2012.
International Search Report and Written Opinion for PCT/US2009/003749 mailed May 19, 2010.
International Preliminary Report on Patentability for PCT/US2011/067993 mailed Jul. 11, 2013.

(56) References Cited

OTHER PUBLICATIONS

International Search Report and Written Opinion for PCT/US2011/067993 mailed May 1, 2012.
International Preliminary Report on Patentability for PCT/US2011/067987 mailed Jul. 11, 2013.
International Search Report and Written Opinion for PCT/US2011/067987 mailed Apr. 30, 2012.
International Preliminary Report on Patentability for PCT/US2011/067991 mailed Jul. 11, 2013.
International Search Report and Written Opinion for PCT/US2011/067991 mailed Apr. 30, 2012.
International Preliminary Report on Patentability for PCT/US2011/067992 mailed Jul. 11, 2013.
International Search Report and Written Opinion for PCT/US2011/067992 mailed Apr. 30, 2012.
International Preliminary Report on Patentability for PCT/US2011/067990 mailed Jul. 11, 2013.
International Search Report and Written Opinion for PCT/US2011/067990 mailed Apr. 30, 2012.
Japanese Office Action for Application No. 2011-93358 mailed Nov. 1, 2012.
Japanese Office Action for Application No. 2011-283904 mailed Jul. 10, 2013.
Katzbauer, Properties and applications of xanthan gum. Polymer Degradation and Stability. 1998;59(1-3): 81-4.
Kirkeby et al., Role of the L-arginine/nitric oxide pathway in relaxation of isolated human enile cavernous tissue and circumflex veins. Acta Physiol Scand., vol. 149, pp. 385-392 (1993).
Klemp et al., Subcutaneous Blood Flow in Early Male Pattern Baldness. J. Invest. Dermatol., 92, pp. 725-726 (1989).
Laan et al., Assessment of female sexual arousal: Response specificity and construct validity. Psychophysiology, vol. 32, pp. 476-485 (1995).
Mathias et al., Topical Capsaicin for Chronic Neck Pain. Am. J. Phys. Rehabil., vol. 74, pp. 39-44 (1995).
Matuszak et al., Thermodynamic Driving Force for Molecular Diffusion—Lattice Density Functional Theory Predictions. J. Non-Equilib. Thermodym. 2006, vol. 31, No. 4, pp. 355-384.
McLatchie et al., The effects of pH on the interaction between capsaicin and the vanilloid receptor in rat dorsal root ganglia neurons. Br J Pharmacol. Feb. 2001;132(4):899-908.
Moody et al., Effects of long-term oral administration of L-arginine on the rat erectile response. The Journal of Urology. 1997;158:942-947.
Nakaki et al., Beneficial Circulato Effect of L-Arginine. Jpn. J. Pharmacol. 66, 167-171 (1994).
Napoli et al., Nitric oxide-releasing drugs. Annu Rev Pharmacol Toxicol. 2003;43:97-123. Epub Jan. 10, 2002.
Owen et al., Topical nitroglycern: A potential treatment for impotence. The Journal of Urology. 1989;143:546-548. Abstract.
Pauly et al., Liposomes containing amino acids and peptides and proteins for skin care. Chemical abstracts, 1998, 113:65069 (Abstract).
Riedel et al., Different mechanisms of L-Arginine induced dilation of brain arterioles in normotensive and hypertensive rats. Brain Res. 1995;671(1):21-6. CA: 122 (11) 130053t [Abstract only].
Rinshyo, Treatment and prevention of diabetic foot ulcer. Shin Jidai no Tonyobyogaku (Studies on Diabetes in a New Age). 2002;4:354-8. Chinese.
Scholermann et al., Clinical and biophysical efficacy of a novel body cream (Eucerin® amino body cream) for aged dry skin containing urea and L-arginine. J Euro Acad Dermatol Venereol. 1998; 11:S270. Abstract P363.
Schölermann et al., Clinical and biophysical efficacy of a novel coenzyme $Q_{10}$ containing anit-wrinkle cream (Eucerin® Q10 active). J Euro Acad Dermatol Venereol. 1998;11:S270. Abstract P364.
Shukla et al., Nitric oxide inhibits wounds collagen synthesis. Mol Cell Biochem. Oct. 1999;200(1-2):27-33.

Singh et al., Response of digital arteries to endothelium dependent and independent vasodilators in patients with Raynaud's phenomenon. European Journal of Clinical Investigation. 1995; 25:182-185.
Singh, Xantham Gum. Printed from: Pharmaceutical Excipients. London: Pharmaceutical Press. 2006. Electronic version. Last revision Aug. 7, 2005. 6 pages.
Sonntag et al., Role of nitric oxide in local blood flow control in the anaesthetized dog. European Journal of Physiology. 1992:194-199.
Suhonen et al., Epidermal cell culture model derived from rat keratinocytes with permeability characteristics comparable to human cadaver skin. Euorpean Journal of Pharmaceutical Sciences 20 (2003) 107-113.
Supplementary European Search Report for EP 98946099.3 mailed Mar. 1, 2006.
Supplementary European Search Report for EP 05723558.2 mailed Feb. 17, 2009.
Supplementary European Search Report for EP 05737763.2 mailed May 12, 2009.
Supplementary European Search Report for EP 05737752.5 mailed Apr. 21, 2009.
The Merck Index, An Encyclopedia of Chemicals, Drugs, and Biologicals, Twelfth Edition, p. 817.
Thompson, Part IV. Exercise as Adjunctive Therapy for Patients with Vascular Disease. Definition and Classification of Peripheral Arterial Disease. In: Exercise & Sports Cardiology. 2001: 372.
Tiso et al., Oral versus topical ibuprofen for chronic knee pain: A prospective randomized pilot study. Pain Physician. Sep./Oct. 2010;13:457-467.
Tseng et al., Increase of nitric oxide production by L-arginine potentiates i.c.v. administered □-endorphin-induced antinociception in the mouse. European Journal of Pharmacology. 1992;212:301-303.
Wang et al., Nitric oxide mediates penile erection in cats. The Journal of Urology. 1994;151:234-237.
Whitmore et al., Acute effect of topical minoxidil on digital blood flow in patients with raynaud's phenomenon. The Journal of Rheumatology. 1995;22(1):50-54.
Writtion Opinion for PCT/US98/19429 mailed Jul. 14, 1999.
Yasuda, The role of nitric oxide in the pathophysiology of diabetic neuropathy. The Autonomic Nervous System. 2003;40:285-289.
Sauermann et al., Caplus Copyright. AN 1995: 648333, abstracting WO 9515147, Jul. 1995.
Extended European Search Report for EP 11852275.4 mailed Dec. 9, 2014.
Extended European Search Report for EP 11854321.4 mailed Dec. 8, 2014.
Extended European Search Report for EP 11853771.1 mailed Dec. 11, 2014.
Extended European Search Report for EP 11853913.9 mailed Dec. 5, 2014.
Extended European Search Report for EP 11854161.4 mailed Dec. 9, 2014.
U.S. Appl. No. 10/590,300, filed Jun. 21, 2007, Fossel.
U.S. Appl. No. 13/860,070, filed Apr. 10, 2013, Fossel.
U.S. Appl. No. 13/977,461, filed Jun. 28, 2013, Fossel.
U.S. Appl. No. 13/977,546, filed Jun. 28, 2013, Fossel.
U.S. Appl. No. 13/977,562, filed Jun. 28, 2013, Fossel.
U.S. Appl. No. 14/067,219, filed Oct. 30, 2013, Fossel.
U.S. Appl. No. 14/067,238, filed Oct. 30, 2013, Fossel.
U.S. Appl. No. 14/067,262, filed Oct. 30, 2013, Fossel.
U.S. Appl. No. 14/067,441, filed Oct. 30, 2013, Fossel.
U.S. Appl. No. 14/071,954, filed Nov. 5, 2013, Fossel.
U.S. Appl. No. 14/072,008, filed Nov. 5, 2013, Fossel.
U.S. Appl. No. 14/682,211, filed Apr. 9, 2015, Fossel.
U.S. Appl. No. 14/724,915, filed May 29, 2015, Fossel.
FLICK, Cosmetic and toiletry formulations. 2nd ed., Noyes Publications, Park Ridge, NJ, 1989, vol. 1, pp. 234, 237.
Griffith et al., A multicentered study of lysine therapy in Herpes simplex infection. Dermatologica. 1978;156(5):257-67. Abstract Only.
Griffith et al., Relation of arginine-lysine antagonism to herpes simplex growth in tissue culture. Chemotherapy. 1981;27(3):209-13. Abstract Only.

(56) References Cited

OTHER PUBLICATIONS

Naito et al., Antiviral effect of arginine against herpes simplex virus type 1. Int J Mol Med. 2009.
U.S. Appl. No. 14/492,394, filed Sep. 22, 2014, Fossel.
U.S. Appl. No. 14/497,910, filed Sep. 26, 2014, Fossel.
U.S. Appl. No. 14/551,153, filed Nov. 24, 2014, Fossel.
EP1182275.4, Dec. 9, 2014, Extended European Search Report.
EP11852275.4, Dec. 8, 2014, Extended European Search Report.
EP11853771.1, Dec. 11, 2014, Extended European Search Report.
EP11853913.9, Dec. 5, 2014, Extended European Search Report.
EP11854161.4, Dec. 9, 2014, Extended European Search Report.
Japanese Office Action for Application No. JP 2013-547682 mailed Nov. 12, 2015.

\* cited by examiner

SYSTEMS AND METHODS FOR TREATMENT OF ALLERGIES AND OTHER INDICATIONS

RELATED APPLICATIONS

This application is a national stage filing under 35 U.S.C. §371 of International Patent Application PCT/US2011/067987, filed Dec. 29, 2011, which claims the benefit of U.S. Provisional Patent Application Ser. No. 61/428,003, filed Dec. 29, 2010, entitled "Systems and Methods for Treatment of Allergies and Other Indications," by E. T. Fossel; and of U.S. Provisional Patent Application Ser. No. 61/428,213, filed Dec. 29, 2010, entitled "Methods and Compositions for Preparing Emulsions for Topical Drug Delivery," by E. T. Fossel. Each of these is incorporated herein by reference in its entirety.

FIELD OF INVENTION

The present invention generally relates to transdermal delivery and, in particular, to the transdermal delivery of $H_1$ antihistamines and other compounds.

BACKGROUND

A histamine antagonist is an agent that inhibits action of histamine via histamine receptors. $H_1$ antihistamines are used as treatment for symptoms of allergies such as runny nose. Allergies are caused by an excessive type 1 hypersensitivity response of the body to allergens, such as pollen released by plants. An allergic reaction, which if severe enough can lead to anaphylaxis, results in excessive release of histamines and other mediators by the body. Other uses of $H_1$ antihistamines help with symptoms of local inflammation that results from various conditions, such as insect stings, even if there is no allergic reaction.

SUMMARY OF THE INVENTION

The present invention generally relates to the transdermal delivery of $H_1$ antihistamines and other compounds. The subject matter of the present invention involves, in some cases, interrelated products, alternative solutions to a particular problem, and/or a plurality of different uses of one or more systems and/or articles.

Several methods are disclosed herein of administering a subject with a composition for prevention or treatment of a particular condition. It is to be understood that in each such aspect of the invention, the invention specifically includes, also, the composition for use in the treatment or prevention of that particular condition, as well as use of the composition for the manufacture of a medicament for the treatment or prevention of that particular condition.

In some embodiments, aspects of the invention relate to compositions for delivering an $H_1$ antihistamine and/or a salt thereof to a subject. In some embodiments, a composition comprises an $H_1$ antihistamine and/or a salt thereof in a hostile biophysical environment for topical delivery to the skin of a subject. In some embodiments, a composition also comprises a nitric oxide donor. In some embodiments, a composition further comprises one or more compounds that stabilize and/or otherwise promote the efficacy of storage and/or delivery (e.g., with or without a nitric oxide donor).

In some embodiments, compositions of the invention increase the efficiency of direct compound delivery to a target site by using transdermal delivery thereby significantly lowering the systemic exposure and reducing potential side effects. For example, a transdermal delivery according to the invention can reduce systemic exposure to less than 10% (e.g., less than 5%, or between 0.1% and 1%, or even less) of the systemic exposure resulting from an oral dosage required for effective delivery of the compound. For example, sedation effects produced by systemic diphenhydramine can be avoided by using a topical formulation of the invention that provides sufficient local levels near the site of topical administration to be effective without producing sedation side-effects associated with the systemic levels that result from oral administration. Also, in some embodiments, compositions of the invention provide for unexpectedly high speeds of action of the compound being delivered (e.g., relative to oral delivery or other delivery techniques used for the compound). Accordingly, in some embodiments, aspects of the invention are useful for rapid therapy when delivery of a therapeutic amount of a compound within a short period of time is required. Topical delivery formulations described herein can deliver a compound to a target tissue more rapidly than an oral formulation, for example. Topical delivery formulations also allow for targeted local delivery of a therapeutically effective amount of compound without requiring a significant systemic increase in the amount of compound. However, it should be appreciated that topical formulations can be used for systemic delivery if so required.

One aspect of the present invention is generally directed to a composition, e.g., a composition for topical delivery to the skin of a subject. In one set of embodiments, the composition includes a nitric oxide donor, a hostile biophysical environment, a stabilization polymer, propylene glycol, a polysorbate surfactant, and an $H_1$ antihistamine and/or a salt thereof.

According to another set of embodiments, at least about 80% by weight of the composition comprises water, at least one chloride salt, a nitric oxide donor, a stabilization polymer, propylene glycol, a polysorbate surfactant, and an $H_1$ antihistamine and/or a salt thereof.

In accordance with yet another set of embodiments, the composition includes a nitric oxide donor, a hostile biophysical environment, and an $H_1$ antihistamine and/or a salt thereof.

The composition, in still another set of embodiments, comprises or consists essentially of water, sodium chloride, a nitric oxide donor, glyceryl stearate, magnesium sulfate and/or magnesium chloride, squalane, a stabilization polymer, isopropyl myristate, oleic acid, propylene glycol, a polysorbate surfactant, and an $H_1$ antihistamine and/or a salt thereof. The composition may also comprise or consist essentially of an antioxidant.

In yet another set of embodiments, the composition comprises or consists essentially of water, sodium chloride, a nitric oxide donor, glyceryl stearate, cetyl alcohol, magnesium sulfate and/or magnesium chloride, squalane, a stabilization polymer, isopropyl myristate, oleic acid, propylene glycol, a polysorbate surfactant, and an $H_1$ antihistamine and/or a salt thereof. The composition may also comprise or consist essentially of an antioxidant.

According to still another set of embodiments, the composition comprises each of the following compounds at concentrations of no more than +20% of the stated concentrations: water at a concentration of about 35% to about 55% by weight, sodium chloride at a concentration of about 2.5% to about 15% by weight, a nitric oxide donor at a concentration of about 2.5% to about 15% by weight, glyceryl stearate at a concentration of about 4% to about 10% by weight, cetyl alcohol at a concentration of about 4% to about 10% by weight, magnesium chloride at a concentration of about 2.5% to about 15% by weight, squalane at a concentration of about 1% to about 8% by weight, a polysorbate surfactant at a concentration of about 0.2% to about 2% by weight, isopropyl myristate at a concentration of about 0.1% to about 5% by weight, oleic acid at a concentration of about 0.1% to about 5% by weight, propylene glycol at a concentration of about 1% to about 10% by weight, a stabilization polymer at a concentration of about 1% to about 10% by weight, and an $H_1$ antihistamine and/or a salt thereof at a concentration of about 0.1% to about 5% by weight. The composition may also comprise an antioxidant at a concentration of about 0.1 to about 1% by weight.

The composition, in yet another set of embodiments, comprises each of the following compounds at concentrations of no more than +20% of the stated concentrations: water at a concentration of about 35% to about 55% by weight, sodium chloride at a concentration of about 2.5% to about 15% by weight, a nitric oxide donor at a concentration of about 2.5% to about 15% by weight, glyceryl stearate at a concentration of about 4% to about 10% by weight, magnesium chloride at a concentration of about 2.5% to about 15% by weight, squalane at a concentration of about 1% to about 8% by weight, a polysorbate surfactant at a concentration of about 0.2% to about 2% by weight, isopropyl myristate at a concentration of about 0.1% to about 5% by weight, oleic acid at a concentration of about 0.1% to about 5% by weight, propylene glycol at a concentration of about 1% to about 10% by weight, a stabilization polymer at a concentration of about 1% to about 10% by weight, and an $H_1$ antihistamine and/or a salt thereof at a concentration of about 0.1% to about 5% by weight. The composition may also comprise an antioxidant at a concentration of about 0.1 to about 1% by weight.

In some embodiments, a composition comprises approximately 7.5% (e.g., 1% to 15%, or more or less) by weight of antihistamine (e.g., diphenhydramine or other antihistamine) in an oil/water emulsion further comprising about 10% sodium chloride, and about 5% magnesium chloride. For example, the antihistamine may be an $H_1$ antihistamine and/or a salt thereof.

In some embodiments, the pH of a composition is optimized to ionize the antihistamine while remaining compatible with acceptable pH ranges for contact with the skin (e.g., within a range of about pH 5 to about pH 8). In some embodiments, a pH at least about 1 pH unit above or below (e.g., at least about 2 pH units above or below) the pKa of diphenhydramine of 9.0 is sufficient to ionize the antihistamine. In some embodiments, a pH of 7 (+/−1.0) is effective. In some embodiments, a pH of 7.2 (e.g., +/−0.5) is particularly effective for diphenhydramine. In some embodiments, a pH at least about 1 pH unit above or below the pKa of an antihistamine may be used, particularly if the pH is within the range of about pH 5.0-8.0 that is particularly compatible for direct topical contact with skin. The antihistamine may be, for instance, an $H_1$ antihistamine and/or a salt thereof, or any antihistamine discussed herein.

According to aspects of the invention, a relatively high salt concentration, for example at least about 2% (e.g., about 5%, about 10% about 15%, about 20% about 25%, about 25-50%, weight %) is useful to provide a hostile biophysical environment that promotes transdermal migration of an antihistamine (e.g., diphenhydramine). In some embodiments, emulsions described herein, for example, containing a stabilization polymer and/or a polysorbate surfactant and/or propylene glycol (or a low molecular weight glycol, or a polyglycol such as polyethylene glycol or other polyglycol—however it should be appreciated that glycols with even numbers of carbons can be toxic, particularly for smaller glycols such as ethylene glycol and butylene glycol, and should be avoided or excluded) are unexpectedly effective at stabilizing the antihistamine in the high salt composition in a form that remains effective for an extended period—for example, retaining rapid transdermal delivery of the antihistamine for at least several weeks or months. In some cases, the antihistamine is an $H_1$ antihistamine (e.g., diphenhydramine) and/or a salt thereof.

In still another set of embodiments, the composition includes a stabilization polymer, propylene glycol, a polysorbate surfactant; and an $H_1$ antihistamine and/or a salt thereof.

In another set of embodiments, at least about 80% by weight of the composition comprises water, at least one chloride salt, a stabilization polymer, propylene glycol, a polysorbate surfactant, an antioxidant, and an $H_1$ antihistamine and/or a salt thereof.

The invention, in accordance with another aspect, is generally directed to a method. In one set of embodiments, the method is a method of applying any of the compositions described herein to a subject, e.g., to the skin of a subject. The method, in accordance with another set of embodiments, includes an act of applying, to a portion of the skin of a subject, a delivery vehicle comprising an $H_1$ antihistamine and/or a salt thereof in a hostile biophysical environment.

In still another set of embodiments, the method includes an act of applying, to at least a portion of the skin of a subject, a composition comprising a nitric oxide donor, a hostile biophysical environment, a stabilization polymer, propylene glycol, a polysorbate surfactant, and an $H_1$ antihistamine and/or a salt thereof.

In another aspect, the present invention encompasses methods of making one or more of the embodiments described herein, for example, a composition comprising an $H_1$ antihistamine. In still another aspect, the present invention encompasses methods of using one or more of the embodiments described herein, for example, a composition comprising an $H_1$ antihistamine. In yet another aspect, the present invention encompasses various uses of a composition including an $H_1$ antihistamine. For example, the composition may be used to treat an allergy.

In some embodiments, aspects of the invention relate to a patch that comprises a composition of the invention (e.g., with or without a nitric oxide donor, and with or without one or more stabilizing compounds). In some embodiments, a composition is in the form of a cream or ointment that is incorporated into the patch. However, other configurations also may be used.

In some embodiments, aspects of the invention relate to methods and formulations for delivering a compound locally at a fraction of the systemic dose required using oral delivery. In some embodiments, a hostile biophysical environment may be evaluated for enhancing local delivery through a topical application. Depending on the therapeutic application, an appropriate delivery configuration (e.g., a combination of compound concentration, hostile biophysical environment, cream, patch, etc.) can be used to reduce the systemic amount of the compound required for an effective therapeutic application.

In some embodiments, aspects of the invention relate to topical formulations and methods that can be used (e.g., when treating skin allergies) to reduce or avoid drowsiness often associated with oral administration of a compound described herein. Topical formulations described herein also are faster acting than oral formulations.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control in the absence of clear error. If two or more documents incorporated by reference include conflicting and/or inconsistent disclosure with respect to each other, then the document having the later effective date shall control.

DETAILED DESCRIPTION

The present invention generally relates to the transdermal delivery of various compounds. In some aspects, transdermal delivery may be facilitated by the use of a hostile biophysical environment. One set of embodiments provides a composition for topical delivery comprising an $H_1$ antihistamine and/or an $H_1$ antihistamine salt, and optionally, a hostile biophysical environment and/or a nitric oxide donor. In some cases, the composition may be stabilized using a combination of a stabilization polymer (such as xanthan gum, KELTROL® BT and/or KELTROL® RD), propylene glycol, and a polysorbate surfactant such as Polysorbate 20, which combination unexpectedly provides temperature stability to the composition, e.g., at elevated temperatures such as at least 40° C. (at least about 104° F.), as compared to compositions lacking one or more of these.

According to aspects of the invention, compositions comprising a relatively high salt composition (e.g., high chloride content) are unexpectedly effective for topical delivery of an $H_1$ antihistamine (including salts thereof), for example diphenhydramine. In some embodiments, a salt-enhanced delivery (e.g., in a composition having at least 2% salt, at least 5% salt, at least 10% salt, at least 15% salt, or higher as described herein) is particularly effective when the pH of the composition is optimized to ionize the compound being delivered (e.g., at least about 80%, at least about 90%, at least about 95%, or about 99% or more) is ionized. It should be appreciated that depending on the pKa of the compound and the pH of the composition, the ionized form may be anionic or cationic (e.g., due to protonation). In some embodiments, a compound may contain several ionizable groups each having a different pKa. In some embodiments, it is sufficient for at least 1, 2, or 3 of the groups to be ionized for the salt-enhanced delivery to be effective. In some embodiments, an ionizable group is sufficiently ionized if the pH of the composition is at least 1 pH unit, or at least 2 pH units (e.g., 1, 1-2, 2-3, or more pH units) below the pKa of the group and it is cationic (due to protonation) below its pKa. Similarly, in some embodiments, an ionizable group is sufficiently ionized if the pH of the composition is at least 1 pH unit, or at least 2 pH units (e.g., 1, 1-2, 2-3, or more pH units) above the pKa of the group and it is anionic (due to deprotonation) above its pKa. In some embodiments, the presence of magnesium chloride, for example at 0.1-5% by weight, can help stabilize composistions containing compounds with relatively high pKas (e.g., above 8.0, above 9.0, above 10.0 or higher). In some embodiments, the pH of a composition may be maintained using a buffer. However, the pH of compositions of the invention are surprisingly stable without a buffer. In some embodiments, a desired pH can be established by titrating the mixture with an acid (e.g., HCl) or a base (e.g., NaOH). The pH of the resulting composition (e.g., when formulated as an emulsion as described herein) can be stable (e.g., sufficiently for the composition to be effective for transdermal delivery) for extended periods of time (e.g., weeks, months, or 1 or more years).

According to other aspects of the invention, a high salt composition containing an $H_1$ antihistamine (including salts thereof) is unexpectedly stable when formulated as an emulsion (e.g., a water in oil emulsion or an oil in water emulsion, for example, including one or more of a stabilization polymer and/or a polysorbate surfactant and/or propylene glycol (or other low molecular weight glycol, or a polyglycol) as described herein). In some embodiments, the pH of the composition comprising the emulsion and high salt concentration is selected to ionize the compound being delivered as described herein.

In some embodiments, topical delivery according to the invention (e.g., topical delivery of an H1 antihistamine (including salts thereof), for example diphenhydramine) provides a surprisingly rapid effect (within about 1-5 minutes) on symptoms (e.g., hives or other allergic rashes or other symptoms). In contrast, current formulations of diphenhydramine take significantly longer (e.g., about 40 minutes or more) to take effect. Accordingly, aspects of the invention provide methods and compositions for delivering an effective treatment to a subject to treat or prevent an allergy. In some embodiments, a topical composition is applied to a region of inflamed skin (or skin that has a rash, or other signs of allergy, including, for example, hives). In some embodiments, a composition is provided to produce relief from symptoms of allergy in less than 1 hour, less than 30 minutes, less than 20 minutes, less than 15 minutes, less than 10 minutes, or less than 5 minutes.

One aspect of the invention provides compositions for the topical delivery of substances such as pharmaceutical agents (e.g., drugs, biological compounds, etc.). The pharmaceutical agents may be applied to the skin of a subject, e.g. a human, to aid in treatment of medical conditions or diseases, and/or the symptoms associated thereof. In some embodiments, the invention provides for the treatment of medical conditions or diseases and/or ailments using pharmaceutical agents (for example, to treat a subject diagnosed with a medical condition or disease, as described herein), and in some cases, the invention provides for the delivery of a minimum amount of pharmaceutical agents to provide effective levels of medication to an effected area topically while limiting side effects. In some cases, the effective dosage of the pharmaceutical agent may be lower than the effective dosage of the pharmaceutical agent when taken orally.

In one set of embodiments, the $H_1$ antihistamine may have a structure:

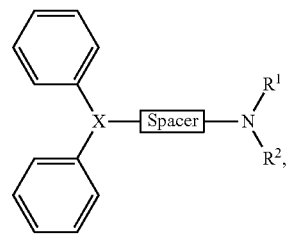

where X is CH, N, C(CH$_3$), or C(OH); the "Spacer" is usually 2-3 carbons in length, and may be linear, ring, branched, saturated or unsaturated; and $R^1$ and $R^2$ each independently may be —H, or a substituted or unsubstituted alkyl group, e.g., —CH$_3$. In some cases, X may be a chiral center. In certain cases, the two aromatic rings can be orientated in different planes; for example, the tricyclic ring system may be slightly puckered and the two aromatic rings may be arranged to lie in different geometrical planes.

Non-limiting examples of $H_1$ antihistamines include, but are not limited to, fexofenadine (pKa of 13.20), cetirizine (pKa of 1.6-2.2, 2.9-3.0, 8.0-8.3) (or levocertrizine), clemastine, diphenhydramine (pKa of 8.2-9.1), doxylamine (pKa of 8.7-9.2), pheniramine (pKa of 4.2, 9.3-9.4), ebastine, chlorpheniramine (pKa of 9.2-9.4), meclizine, embramine, dexchlorpheniramine, and loratadine (pKa of 4.9-5.0). The structures of these compounds are respectively shown below:

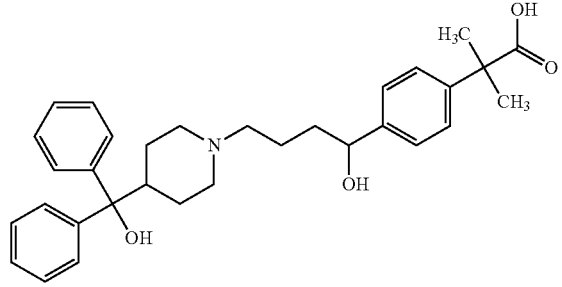

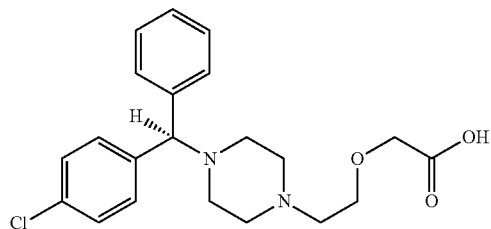

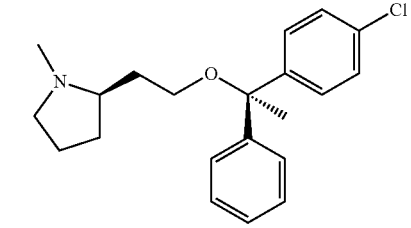

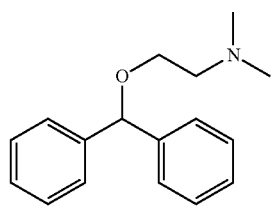

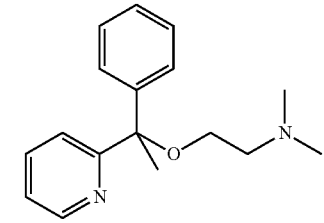

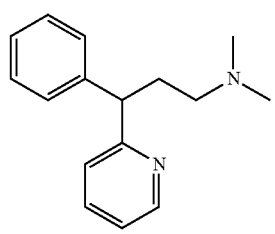

-continued

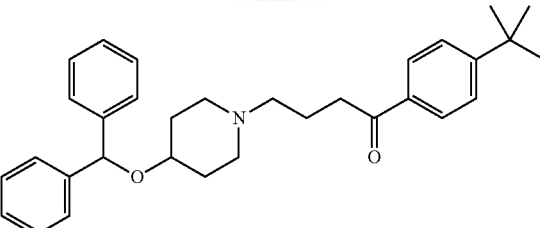

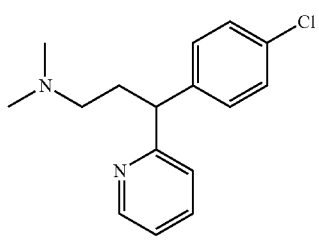

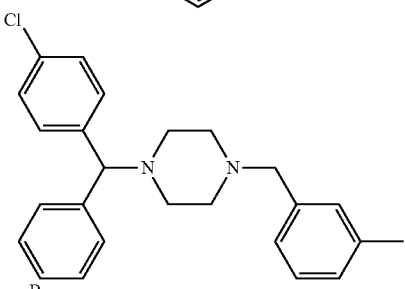

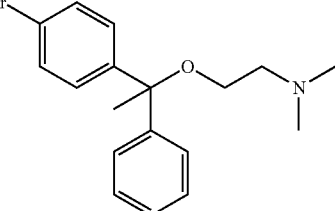

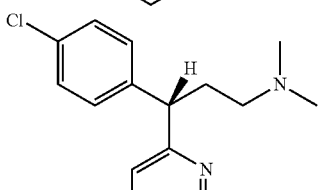

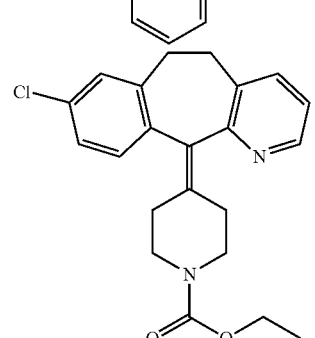

Accordingly, various aspects of the invention are directed to compositions including an $H_1$ antihistamine for transdermal delivery or topical application to a subject. Besides an $H_1$ antihistamine, other compounds such as salts or derivatives of $H_1$ antihistamines are also included in other embodiments; thus, it should be understood that in any embodiment described herein using an $H_1$ antihistamine, this is by way of example only, and other embodiments of the invention are directed to $H_1$ antihistamine salts, $H_1$ antihistamine derivatives, etc., instead of and/or in addition to $H_1$ antihistamines.

$H_1$ antihistamines or other pharmaceutical agents (e.g., salts or derivatives of $H_1$ antihistamines, etc.) may be present at any suitable concentration. For instance, in some cases, the pharmaceutical agent may be present at a concentration of at least about 0.1%, at least about 0.3%, at least about 0.5%, at least about 0.7%, at least about 1%, at least about 2%, at least about 3%, at least about 4%, at least about 5%, at least about 6%, at least about 7%, at least about 7.5%, at least about 8%, at least about 9%, or at least about 10% by weight of the composition. In certain embodiments, the pharmaceutical agent may be present at a concentration of no more than about 1%, no more than about 2%, no more than about 3%, no more than about 4%, no more than about 5%, no more than about 6%, no more than about 7%, no more than about 8%, no more than about 9%, no more than about 10%, no more than about 12%, no more than about 15%, or no more than about 20% by weight of the composition. In addition, the pharmaceutical agent may be present in native form and/or as one or more salts. For example, if an $H_1$ antihistamine is present, it may be used in its native form, and/or as one or more salts, e.g., the sodium salt, the potassium salt, the magnesium salt, the lysine salt, the arginine salt, the hydrochloride salt, the tannate salt, the citrate salt, the acefylline salt, the maleate salt, etc. of an $H_1$ antihistimate, e.g., fexofenadine, cetirizine (or levocertrizine), clemastine, diphenhydramine, doxylamine, pheniramine, ebastine, chlorpheniramine, meclizine, embramine, dexchlorpheniramine, loratadine, etc. For salt forms of the pharmaceutical agent, "by weight of the composition" includes the entire salt form of the pharmaceutical agent, e.g., the agent itself as well as any counterions such as sodium, potassium, etc. The amount of the pharmaceutical agent may be determined in a composition, for example, using techniques such as HPLC or HPLC/MS that are known to those of ordinary skill in the art.

Many $H_1$ antihistamines are readily commercially available. In some cases, the $H_1$ antihistamine may be obtained as a racemic mixture, for example, for fexofenadine (e.g., (R)-fexofenadine and (S)-fexofenadine), or cetirizine (e.g., (R)-cetirizine and (S)-cetirizine). However, in other cases, one of the enantiomers may be present in an amount greater than the other. For example, at least about 60%, at least about 70%, at least about 80%, at least about 90%, or at least about 95% of the $H_1$ antihistamine within the composition may be present as one of the enantiomers. Techniques for preparing or separating racemic $H_1$ antihistamines are known; see, for example, Fang, et al., "An Efficient and Facile Synthesis of Racemic and Optically Active Fexofenadine," *Tetrahedron Lett.*, 39:2701-2704, 1998; Liu, et al., "Direct Separation of the Enantiomers of Cetirizine and Related Compounds by Reversed-Phase Chiral HPLC," *Chromatographia*, 56:233-235, 2002; Pflum, "A Large-Scale Synthesis of Enantiomerically Pure Cetirizine Dihydrochloride Using Preparative Chiral HPLC," *Org. Proc. Res. Dev.*, 5:110-115, 2001.

The composition may also comprise a nitric oxide donor in some embodiments, for example, L-arginine and/or L-arginine hydrochloride. In some cases, such a nitric oxide donor may be used to increase localized blood flow at the site where the composition is applied, which may enhance delivery of the pharmaceutical agent. The nitric oxide donor may be present at any suitable concentration within the composition. For instance, in some cases, the nitric oxide donor is present at a concentration of at least about 1%, at least about 2%, at least about 3%, at least about 4%, at least about 5%, at least about 6%, at least about 7%, at least about 7.5%, at least about 8%, at least about 9%, or at least about 10% by weight of the composition. In some cases, one or more nitric oxide donors (e.g., 2, 3, 4, 5, 6, 7, 8, 9, 10, etc. nitric oxide donors) may be used. In some cases, there may be no more than 3, 5, 7, or 10 nitric oxide donors present within the composition.

A "nitric oxide donor," as used herein, is a compound that is able to release nitric oxide and/or chemically transfer the nitric oxide moiety to another molecule, directly or indirectly, for example, through a biological process. The nitric oxide donor may release nitric oxide into the skin, and/or tissues such as muscles and/or elements of the circulatory system in close proximity to the surface of the skin. Non-limiting examples of nitric oxide donors include arginine (e.g., L-arginine and/or D-arginine), arginine derivatives (e.g., L-arginine hydrochloride and/or D-arginine hydrochloride), nitroglycerin, polysaccharide-bound nitric oxide-nucleophile adducts, N-nitroso-N-substituted hydroxylamines, 1,3-(nitrooxymethyl)phenyl-2-hydroxybenzoate, etc., and/or any combination of these and/or other compounds.

Besides L-arginine and L-arginine hydrochloride, other non-limiting examples of nitric oxide donors include D,L-arginine, D-arginine, or alkyl (e.g., ethyl, methyl, propyl, isopropyl, butyl, isobutyl, tert-butyl, etc.) esters of L-arginine and/or D-arginine (e.g., a methyl ester, an ethyl ester, a propyl ester, a butyl ester, etc.) and/or salts thereof, as well as other derivatives of arginine and other nitric oxide donors. For instance, non-limiting examples of pharmaceutically acceptable salts include hydrochloride, glutamate, butyrate, or glycolate (e.g., resulting in L-arginine glutamate, L-arginine butyrate, L-arginine glycolate, D-arginine hydrochloride, D-arginine glutamate, etc.). Still other examples of nitric oxide donors include L-arginine-based compounds such as, but not limited to, L-homoarginine, N-hydroxy-L-arginine, nitrosylated L-arginine, nitrosylated L-arginine, nitrosylated N-hydroxy-L-arginine, nitrosylated N-hydroxy-L-arginine, citrulline, ornithine, linsidomine, nipride, glutamine, etc., and salts thereof (e.g., hydrochloride, glutamate, butyrate, glycolate, etc.), and/or any combination of these and/or other compounds. Still other non-limiting examples of nitric oxide donors include S-nitrosothiols, nitrites, 2-hydroxy-2-nitrosohydrazines, or substrates of various forms of nitric oxide synthase. In some cases, the nitric oxide donor may be a compound that stimulates endogenous production of nitric oxide in vivo. Examples of such compounds include, but are not limited to, L-arginine, substrates of various forms of nitric oxide synthase, certain cytokines, adenosine, bradykinin, calreticulin, bisacodyl, phenolphthalein, OH-arginine, or endothelein, and/or any combination of these and/or other compounds.

Accordingly, it should be understood that, in any of the embodiments described herein that describe L-arginine and/or L-arginine hydrochloride, other nitric oxide donors may also be used instead, or in combination with, L-arginine and/or L-arginine hydrochloride, in other embodiments of the invention.

In some cases, the concentration of the nitric oxide donor within the composition may be tailored to have a duration of effective treatment of at least about 3 hours, at least about 5 hours, or at least about 8 hours or more in certain instances. The duration may also be controlled, for instance, by controlling the concentration of a penetrating agent used in conjunction with the nitric oxide donor. Penetration agents are discussed in detail herein. The actual concentration for a particular application can be determined by those of ordinary skill in the art using no more than routine experimentation, for example, by measuring the amount of transport of the nitric oxide donor as a function of concentration in vitro across cadaver skin or suitable animal models, skin grafts, synthetic model membranes, human models, or the like.

As a particular non-limiting example, in certain embodiments, nitric oxide is provided using L-arginine, for example, at a concentration of at least about 0.5% by weight (wt % or w/v) of L-arginine (optionally with one or more penetrating agents as discussed herein, for example, a penetrating agent able to create a hostile biophysical environment), at least about 0.75 wt %, at least about 1 wt %, at least about 2 wt %, at least about 3 wt %, at least about 5 wt %, at least about 7 wt %, at least about 10 wt %, or at least about 15 wt %. The L-arginine may be present in a suitable delivery vehicle, such as a cream or a lotion. L-arginine may be particularly useful in some cases due to its low toxicity, its high solubility, and/or its low cost. Other examples of nitric oxide donors are discussed in International Patent Application No. PCT/US2005/005726, filed Feb. 23, 2005, entitled "Topical Delivery of a Nitric Oxide Donor to Improve Body and Skin Appearance," by E. T. Fossel, published as WO 2005/081964 on Sep. 9, 2005, incorporated herein by reference.

Without wishing to be bound to any theory, it is generally believed that the flow of the pharmaceutical agent across the skin may slow as it builds up within the tissue. Fick's first law of diffusion suggests that when the concentration inside becomes substantially equal to that outside, passive flow stops. The increased local blood flow may prevent or at least decrease the stoppage of the flow of the pharmaceutical agent. Thus, when the composition is applied to the skin, the pharmaceutical agent exits the vehicle into the tissue more readily, as the pharmaceutical agent is dispersed by flow and does not build up in concentration in the tissue. Thus, in certain embodiments, pharmaceutical agents may be introduced into the skin, for example, an $H_1$ antihistamine and/or a salt or derivative of an $H_1$ antihistamine, such as fexofenadine, cetirizine (or levocertrizine), clemastine, diphenhydramine, doxylamine, pheniramine, ebastine, chlorpheniramine, meclizine, embramine, dexchlorpheniramine, or loratadine. Accordingly, the composition may be delivered locally and/or systemically; initially, much of the delivery is at first local (i.e., through the skin), but in some cases, the pharmaceutical agents may also be distributed systemically, e.g., upon reaching the blood supply.

The composition may also comprise a hostile biophysical environment to an $H_1$ antihistamine in some embodiments. In a hostile biophysical environment, the environment surrounding the pharmaceutical agent (e.g., an $H_1$ antihistamine, etc.) may be such that the pharmaceutical agent is in a chemically and/or energetically unfavorable environment, relative to the skin (e.g., the chemical potential and/or the free energy of the pharmaceutical agent within the hostile biophysical environment is significantly greater than the chemical potential and/or the free energy of the pharmaceutical agent within the skin, thus energetically favoring transport into the skin), especially the stratum corneum.

Examples of such compositions are discussed in International Patent Application No. PCT/US2005/013228, filed Apr. 19, 2005, entitled "Transdermal Delivery of Beneficial Substances Effected by a Hostile Biophysical Environment," by E. Fossel, published as WO 2005/102282 on Nov. 3, 2005, incorporated herein by reference. Other techniques for hostile biophysical environments are discussed in detail herein. Accordingly, certain embodiments of the invention are generally directed to compositions for topical delivery to the skin of a subject comprising a nitric oxide donor, a hostile biophysical environment, and a pharmaceutical agent such as an $H_1$ antihistamine, or a salt or a derivative of an $H_1$ antihistamine, or the like.

A hostile biophysical environment of the invention can comprise, in various embodiments, high ionic strength, a high concentration of osmotic agents such as ureas, sugars, or carbohydrates, a high pH environment (e.g., greater than about 7, greater than about 8, greater than about 9, greater than about 10, greater than about 11, greater than about 12, or greater than about 13), a low pH environment (less than about 5, less than about 4, less than about 3 or less than about 2), highly hydrophobic components, or highly hydrophilic components or other substances that cause an increase in the chemical potential and/or free energy of the pharmaceutical agent, or any combination of two or more of these and/or other compounds. A hydrophobic component may, in some embodiments, have an octanol-water partition coefficient of at least about 100, at least about 1000, at least about $10^4$, at least about $10^5$, or more in some cases. Similarly, a hydrophilic component may have an octanol-water partition coefficient of less than about 0.01, less than about $10^{-3}$, less than about $10^{-4}$, or less than about $10^{-5}$ in some cases.

In some cases, the composition defines the biophysical hostile environment. In other cases, a pharmaceutical agent may be packaged in such a way that it is carried into tissue and/or its charge is neutralized by derivitization and/or by forming a neutral salt. Examples of biophysically hostile environments include, but are not limited to, high ionic strength environments (e.g., by the addition of ureas, sugars, carbohydrates, and/or ionic salts such as lithium chloride, sodium chloride, potassium chloride, calcium chloride, magnesium chloride, choline chloride, sodium fluoride, lithium bromide, etc.), as well as combinations of these and/or other agents, for instance at high ionic strengths (for example, greater than about 0.25 M, greater than about 1 M, greater than about 2 M, greater than about 3 M, greater than about 5 M, greater than about 10 M, greater than about 15 M, greater than about 20 M, greater than about 25 M, etc., or in some cases, between about 0.25 M and about 15 M, between about 5 M and about 15 M, between about 10 M and about 15 M, etc.); high or low pH environments (e.g., by adding pharmaceutically acceptable acids or bases, for example, such that the pH is between about 3 and about 7, between about 3 and about 6, between about 3 and about 5, between about 4 and 8, between about 5 and about 8, between about 5 and 8.5, between about 7 and about 11, between about 8 and about 11, between about 9 and about 11, etc.); or highly hydrophobic environments (e.g., by decreasing water content and increasing lipid, oil and/or wax content of the environment). In some embodiments, the ionic strength is any amount greater than two times the physiological ionic strength of blood. The ionic strength of a composition can be readily controlled in certain embodiments by controlling the amounts or concentrations of one or more of the salts present in the composition, e.g., by controlling the amount of sodium chloride, magnesium chloride, choline chloride, etc., and/or other salts.

Other highly charged molecules such as polylysine, polyglutamine, polyaspartate, etc., or copolymers of such highly charged amino acids may also be used in certain embodiments to create the hostile biophysical environment. Non-limiting examples of delivery vehicles which would be carried into tissue includes liposomes or emulsions of collagen, collagen peptides or other components of skin or basement membrane. Non-limiting examples of neutralization of charge include delivery of the pharmaceutical agent in the form or an ester or salt which is electronically neutral. In some embodiments, the hostile biophysical environment may include any two or more of these conditions. For instance, the hostile biophysical environment may include high ionic strength and a high pH or a low pH, a highly hydrophobic environment and a high pH or a low pH, a highly hydrophobic environment that includes liposomes, or the like.

A hostile biophysical environment may also be created in some embodiments by placing a pharmaceutical agent that is relatively highly charged into a hydrophobic, oily environment such as in an oil-based cream or lotion containing little or no water. Absorption may further be aided by combining the use of hostile biophysical environments with the use of penetrating agents, as further described herein.

In one set of embodiments, the composition may be present as an emulsion. As known by those of ordinary skill in the art, an emulsion typically includes a first phase (e.g., a discontinuous phase) contained within a second fluid phase (e.g., a continuous phase). The pharmaceutical agent (e.g., an $H_1$ antihistamine) may be present in either or both phases. In addition, other materials such as those described herein may be present in the same phase as the pharmaceutical agent.

In some embodiments, an emulsion may be prepared to contain a drug (or other pharmaceutical agent) of interest in a hostile biophysical environment, and optionally one or more of a stabilization polymer, propylene glycol, and/or a polysorbate surfactant. An emulsion may also comprise a nitric oxide donor in some embodiments, for example, L-arginine and/or L-arginine hydrochloride.

In some embodiments, various aspects of the invention relate to methods and compositions for preparing and/or manufacturing drug formulations for topical delivery. In one set of embodiments, the present invention is generally directed to emulsions that contain one or more drugs or other pharmaceutical agents described herein for topical application. In some embodiments, certain aspects of the invention are useful for preparing emulsions that contain one or more drugs (or other pharmaceutical agents) in a hostile biophysical environment. In some embodiments, the hostile biophysical environment is a high salt concentration (e.g., a high concentration of one or more salts), for example, as described herein.

In some embodiments, an emulsion is prepared by mixing a first aqueous preparation (e.g., a water phase) with a second non-aqueous preparation (e.g., an oil or lipid phase). Drugs or other pharmaceutical agents that are water-soluble may be added to the first aqueous preparation (e.g., prior to mixing with the second non-aqueous preparation). Drugs or other pharmaceutical agents that are water insoluble (or relatively water insoluble) may be added to the second non-aqueous preparation (e.g., prior to mixing with the first aqueous preparation). Drugs or other pharmaceutical agents that are partially water soluble may be added to one phase, or may be split between the two phases prior to mixing. The split between the two phases will depend on the amount of drug (or other pharmaceutical agent) that is being added, the composition (e.g., the nature and the amount of other chemicals or agents) of the first and second preparations, the pH, the temperature, other physical or chemical factors, and/or a combination thereof. For example, if a drug of interest is soluble at a 1% level in the aqueous (e.g., water or buffer) phase, but a 2% level of the drug is required in the emulsion, then the drug may also be added to the non-aqueous (e.g., lipid) phase at a 1% level. In some embodiments, a drug that is less than 1% soluble in an aqueous phase is provided in the non-aqueous phase prior to mixing. However, it should be appreciated that other percentages and/or splits between the two phases may be used.

In some embodiments, the pH of one or both of the first and second preparations is adjusted to optimize the solubility of the drug being used. In some embodiments, a high salt concentration is used. In order to prevent a high salt concentration from breaking down an emulsion, one or more emulsifying agents may be used in some cases. In some embodiments, the mixing time may be adjusted to promote appropriate mixing and/or emulsion formation.

In some embodiments, the temperature of the first and/or second preparation may be controlled to promote solubility, mixing, and/or emulsion formation. In some embodiments, the temperature of one or both preparations and/or of the mixing may be set at 25° C. or higher (e.g., 30° C. or higher, 40° C. or higher, 50° C. or higher, 60° C. or higher, 70° C. or higher, or 80° C. or higher). For example, the temperature may be at between 30° C. and 90° C., between 40° C. and 80° C., at around 50° C., at around 60° C., or at around 70° C.

It should be appreciated that methods and compositions of the invention may be used with any suitable drug or pharmaceutical agent. In some embodiments, for example, an oral drug may be formulated for topical delivery using one or more compositions or methods described herein. A topical formulation may be useful to deliver a locally effective amount of a drug (or other pharmaceutical agent) to a subject (e.g., a human) without causing unwanted side effects associated with systemic levels required for effectiveness when the drug is administered orally. Accordingly, a topical formulation may be useful to deliver an amount of a drug that is sufficient to cause a desired effect (e.g., a therapeutic effect) but that is lower than the total amount of the drug that would be administered to a subject (e.g., a human) if it were provided orally.

Emulsions of the invention may be packaged using any suitable format (e.g., in a tube, a pump-actuated container, or any other suitable form), in certain embodiments of the invention. For example, in some embodiments, an emulsion may be added to a surface of a patch or bandage. The emulsion may also be applied to the skin of a subject as a cream, gel, liquid, lotion, spray, aerosol, or the like.

Methods and compositions such as any of those discussed herein may be used to prepare a composition that is sterile or that has a low microbial content, in some embodiments.

In some aspects of the invention, a composition of the invention is administered to a subject using a delivery vehicle such as a cream, gel, liquid, lotion, spray, aerosol, or transdermal patch. In one set of embodiments, a composition of the invention may be applied or impregnated in a bandage or a patch applied to the skin of a subject. In some embodiments, a patch has a skin contacting portion made of any suitable material that is covered or impregnated with a cream or emulsion described herein, wherein the skin contacting portion may be supported by a backing, one or both of which may have an adhesive segment or other configuration for attaching to the skin surface of a subject. A "subject," as used herein, means a human or non-human animal. Examples of subjects include, but are not limited to, a mammal such as a dog, a cat, a horse, a donkey, a rabbit, a cow, a pig, a sheep, a goat, a rat (e.g., *Rattus Norvegicus*), a mouse (e.g., *Mus musculus*), a guinea pig, a hamster, a primate (e.g., a monkey, a chimpanzee, a baboon, an ape, a gorilla, etc.), or the like. Such delivery vehicles may be applied to the skin of a subject, such as a human subject. Examples of delivery vehicles are discussed herein. The delivery vehicle may promote transfer into the skin of an effective concentration of the nitric oxide donor and/or the pharmaceutical agent, directly or indirectly. For instance, the delivery vehicle may include one or more penetrating agents, as further described herein. Those of ordinary skill in the art will know of systems and techniques for incorporating a nitric oxide donor and/or a pharmaceutical agent within delivery vehicles such as a cream, gel, liquid, lotion, spray, aerosol, or transdermal patch. In some cases, the concentration of the nitric oxide donor, and/or a pharmaceutical agent in the delivery vehicle can be reduced with the inclusion of a greater amount or concentration of penetrating agent, or increased to lengthen the beneficial effect. In one set of embodiments, the nitric oxide donor and/or the pharmaceutical agent may be used in conjunction with an adjunct, such as theophylline (for example, at 10% weight by volume).

Other materials may be present within the delivery vehicle, for example, buffers, preservatives, surfactants, etc. For instance, the cream may include one or more of water, mineral oil, glyceryl stereate, squalene, propylene glycol stearate, wheat germ oil, glyceryl stearate, isopropyl myristate, steryl stearate, polysorbate 60, propylene glycol, oleic acid, tocopherol acetate, collagen, sorbitan stearate, vitamin A and D, triethanolamine, methylparaben, aloe vera extract, imidazolidinyl urea, propylparaben, PND, and/or BHA.

As specific non-limiting examples, a cream may have one or more of (w/v): water (20-80%), white oil (3-18%), glyceryl stearate (0.25-12%), squalene (0.25-12%), cetyl alcohol (0.1-11%), propylene glycol stearate (0.1-11%), wheat germ oil (0.1-6%), polysorbate 60 (0.1-5%), propylene glycol (0.05-5%), collagen (0.05-5%), sorbitan stearate (0.05-5%), vitamin A (0.02-4%), vitamin D (0.02-4%), vitamin E (0.02-4%), triethanolamine (0.01-4%), methylparaben (0.01-4%), aloe vera extract (0.01-4%), imidazolidinyl urea (0.01-4%), propylparaben (0.01-4%), BHA (0.01-4%), L-arginine hydrochloride (0.25-25%), sodium chloride (0.25-25%), magnesium chloride (0.25-25%), and/or choline chloride (0.25-25%). The percentages of each compound can vary (or the compound may be absent in some cases), for example, 1%, 2%, 3%, 4%, 5%, 6%, 7%, 8%, 9%, 10%, 11%, 12%, 13%, 14%, 15%, 20%, etc.

In another embodiment, the cream may include a pharmaceutical agent, for instance, an $H_1$ antihistamine, and one or more of the following, in any suitable amount: water (e.g., 20-80%), L-arginine hydrochloride (e.g., 0-25%), sodium chloride (e.g., 0-25%), potassium chloride (e.g., 0-25%), glyceryl steareate (e.g., 0-15%), cetyl alcohol (e.g., 0-15%), squalene (e.g., 0-15%), isopropyl mysterate (e.g., 0-15%), oleic acid (e.g., 0-15%), Tween 20 (e.g., 0-10%), and/or butanediol (e.g., 0-10%). The percentages of each compound can vary (or the compound may be absent in some cases), for example, 1%, 2%, 3%, 4%, 5%, 6%, 7%, 8%, 9%, 10%, 11%, 12%, 13%, 14%, 15%, 20%, etc.

In some embodiments, the cream may include a pharmaceutical agent, and one or more ionic salts at a concentration at least sufficient to produce a hostile biophysical environment with respect to the pharmaceutical agent. For example, the cream may include one or more of (w/v): a charged and/or hydrogen bonding entity (0.001-30%), choline chloride (1-30%), sodium chloride (2-30%), and/or magnesium chloride (1-20% w/v). In another example, the cream may include one or more of (w/v): L-arginine hydrochloride (2.5-25%), choline chloride (10-30%), sodium chloride (5-20%), and/or magnesium chloride (5-20%). In still another example, the cream may include one or more of (w/v): creatine (0.001-30%), inosine (0.001-30%), choline chloride (1-30%), sodium chloride (2-30%), magnesium chloride (1-20%), L-arginine (0.1-25%), and/or theophylline (0.1-20%). In some cases, the cream may also contain L-arginine hydrochloride (0-12.5% w/v) and/or theophylline (0-10% w/v). The percentages of each compound can vary (or the compound may be absent in some cases), for example, 1%, 2%, 3%, 4%, 5%, 6%, 7%, 8%, 9%, 10%, 11%, 12%, 13%, 14%, 15%, 20%, etc. In these examples, choline chloride, sodium chloride, and/or magnesium chloride can be used to provide a high ionic strength environment.

In some embodiments, the composition may include an antioxidant, which may be able to reduce or inhibit the oxidation of other molecules within the composition. Examples of suitable antioxidants include, but are not limited to, glutathione, vitamin C, and vitamin E as well as enzymes such as catalase, superoxide dismutase and various peroxidases. The antioxidant may be present in any suitable concentration. For example, the antioxidant may be present at a concentration of at least about 0.1%, at least about 0.3%, at least about 0.5%, at least about 0.7%, at least about 1%, at least about 2%, at least about 3%, at least about 4%, or at least about 5% by weight of the composition. In certain embodiments, the pharmaceutical agent may be present at a concentration of no more than about 0.2%, no more than about 0.5%, no more than about 1%, no more than about 2%, no more than about 3%, no more than about 4%, or no more than about 5% by weight of the composition.

The composition may also be light-sensitive, in certain embodiments. Thus, in some cases, the composition may be contained within a dark or opaque container. In certain embodiments, the composition is also prepared under low-light conditions.

Another set of embodiments is generally directed to compositions having relatively high temperature stability. For example, the composition may be stable at elevated temperatures such as at least 40° C. (at least about 104° F.) for periods of time of at least about a day. In some embodiments, for instance, a composition of the present invention may further include a stabilization polymer, propylene glycol, and a polysorbate surfactant. Non-limiting examples of stabilization polymers include xanthan gum, KELTROL® BT and/or KELTROL® RD; an example of a polysorbate surfactant is Polysorbate 20. Additional examples are discussed herein.

Such a combination of components to create high temperature stability are surprising, since compositions involving any two of these components (but not the third) were found to lack such high temperature stabilization properties. It is not currently known why this combination of components is remarkably effective at facilitating relatively high temperature stability of the compositions discussed herein, as these components are not known to participate in any significant chemical reactions with each other, and high temperature stability is greatly reduced when one of the components is removed. In addition, propylene glycol is not known to work in pharmaceutical compositions as a stabilizing agent.

For instance, in one set of embodiments, a composition may be determined to be one that has high temperature stability by determining whether the composition exhibits phase separation over a relatively long period of time, e.g., over at least an hour, at least about 2 hours, at least a day, at least about a week, at least about 4 weeks, etc. For example, in some embodiments, a composition is exposed to ambient temperature and pressure for at least 1 hour, and the composition is then analyzed to determine whether the composition exhibits phase separation or a change in phase. A stable compound is one that exhibits no phase separation, whereas an unstable compound may exhibit phase separation. Such stability may be useful, for example, for storage of the composition, transport of the composition, shelf life, or the like.

As used herein, a "stabilization polymer" is a polymer that comprises xanthan gum, a xanthan gum derivative, and/or a xanthan gum equivalent, for example, KELTROL® BT and/or KELTROL® RD, KELZAN® XC, KELZAN® XCD, KELZAN® D, KELZAN® CC, XANTURAL® 180, XANTURAL® 75, or the like, all of which can be obtained commercially from various suppliers. In some embodiments, combinations of these and/or other polymers are also possible. In some cases, the stabilization polymer is chosen to be one which is at least generally regarded as safe for use in humans. In addition, in certain embodiments, the stabilization polymer is produced synthetically, and/or one which has been purified to some degree. The stabilization polymer may have any suitable molecular weight, for example, at least about 1 million, at least about 2 million, at least about 5 million, at least about 10 million, at least about 25 million, or at least about 50 million.

The stabilization polymer may be present at any suitable concentration within the composition. For example, the stabilization polymer may be present at a concentration of at least about 0.1%, at least about 0.2%, at least about 0.3%, at least about 0.4%, at least about 0.5%, at least about 0.6%, at least about 0.7%, at least about 0.8%, at least about 0.9%, or at least about 1% by weight of the composition. In some embodiments, the stabilization polymer may be present at a concentration of no more than about 0.1%, no more than about 0.2%, no more than about 0.4%, no more than about 0.6%, no more than about 0.8%, no more than about 1%, no more than about 2%, no more than about 3%, no more than about 4%, no more than about 5%, no more than about 7%, no more than about 10%, no more than about 12%, no more than about 15%, or no more than about 20% by weight of the composition. In some cases, more than one stabilization polymer may be present, and each stabilization polymer may be present in any suitable amount. As a specific example, in certain embodiments, the stabilization polymer consists essentially of KELTROL® BT and/or KELTROL® RD. In certain instances, the stabilization polymer may have a fixed ratio of KELTROL® BT and/or KELTROL® RD, for example, 1:1 or 3:5 by weight. In another example, the KELTROL® BT may be present at a concentration of about 0.3% by weight and the KELTROL® RD may be present at a concentration of 0.5% by weight of the composition, or one or both of these may be present at one of the other concentrations described above. Combinations of these and/or other stabilization polymers are also contemplated in other embodiments, e.g., KELTROL® BT and xanthan gum, KELTROL® RD and xanthan gum, etc. In some cases, thickening agents can be used instead of, or in conjunction with a stabilization polymer. Many thickening agents can be obtained commercially. Thickening agents include those used in the food industry, or are GRAS agents (generally regarded as safe), e.g., alginin, guar gum, locust bean gum, collagen, egg white, furcellaran, gelatin, agar, and/or carrageenan, as well as combinations of these and/or other stabilization polymers. It should thus be appreciated that, in the specification herein, references to stabilization polymers, in other embodiments, should be understood to also include thickening agents in conjunction or instead of stabilization polymers, Propylene glycol can be obtained commercially, and can be present as any stereoisomer or racemic mixture of isomers. It may also be present at any suitable concentration. For instance, propylene glycol may be present at a concentration of at least about 1%, at least about 2%, at least about 3%, at least about 4%, at least about 5%, at least about 6%, at least about 7%, at least about 8%, at least about 9%, or at least about 10% by weight of the composition. In some embodiments, propylene glycol may be present at a concentration of no more than about 2%, no more than about 4%, no more than about 6%, no more than about 8%, no more than about 10%, no more than about 12%, no more than about 15%, no more than about 20%, or no more than about 25% by weight of the composition. In some cases, other glycols can be used in conjunction or instead of propylene glycol, such as butylene glycol. Accordingly, it should thus be appreciated that, in the specification herein, references to propylene glycol, in other embodiments, should be understood to also include other glycols (e.g., a low molecular weight glycol, or a polyglycol, as described herein) in conjunction or instead of propylene glycol.

In addition, a polysorbate surfactant can also be present any suitable concentration within the composition. For instance, in some cases, the polysorbate surfactant may be present at a concentration of at least about 1%, at least about 2%, at least about 3%, at least about 4%, at least about 5%, at least about 6%, at least about 7%, at least about 8%, at least about 9%, or at least about 10% by weight of the composition. In certain embodiments, the polylsorbate surfactant may be present at a concentration of no more than about 2%, no more than about 4%, no more than about 6%, no more than about 8%, no more than about 10%, no more than about 12%, no more than about 15%, no more than about 20%, or no more than about 25% by weight of the composition A "polysorbate surfactant," as used herein, is a surfactant comprising a polysorbate. For example, the surfactant may comprise sorbitan monolaurate, sorbitan monopalmitate, sorbitan monostearate, sorbitan monooleate, or another sorbitan salt. In some cases, the polysorbate surfactant has a molecular formula:

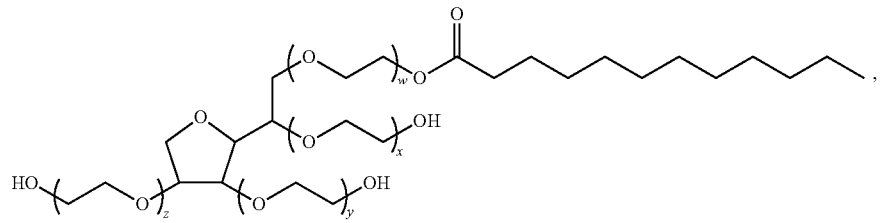

where w, x, y, and z are any suitable positive integers. w, x, y, and z may also each be independently the same or different. In one set of embodiments, w+x+y+z is 20 (e.g., as in Polysorbate 20). In some cases, other polymeric sugars can be used instead of, or in conjunction with, a polysorbate surfactant. Thus, it should be appreciated that, in the specification herein, references to a polysorbate surfactant are by way of example, and in other embodiments, it should be understood that references to a polysorbate surfactant may include other polymeric sugars in conjunction or instead of a polysorbate surfactant.

In some cases, the composition may have a fixed ratio of the stabilization polymer to propylene glycol to the polysorbate surfactant. For instance, the ratio of these may be about 1:1:1, about 1:6:3, about 1:6:2, about 1:7:2, about 1:7:3, about 1.5:1:1, about 1.5:6:3, about 1.5:6:4, about 1:6:2.5, about 1:6.25:2.5, about 1:6.25:2.5, etc. As mentioned above, such ratios may be useful, in certain embodiments of the invention, in providing temperature stability to the composition.

In certain aspects of the invention, a pharmaceutical agent may be combined with a penetrating agent, i.e., an agent that increases transport of the pharmaceutical agent into the skin, relative to transport in the absence of the penetrating agent. In some embodiments, the penetrating agent may define and/or be combined with a hostile biophysical environment. Examples of penetrating agents include oleoresin capsicum or its constituents, or certain molecules containing heterocyclic rings to which are attached hydrocarbon chains.

Non-limiting examples of penetrating agents include, but are not limited to, cationic, anionic, or nonionic surfactants (e.g., sodium dodecyl sulfate, polyoxamers, etc.); fatty acids and alcohols (e.g., ethanol, oleic acid, lauric acid, liposomes, etc.); anticholinergic agents (e.g., benzilonium bromide, oxyphenonium bromide); alkanones (e.g., n-heptane); amides (e.g., urea, N,N-dimethyl-m-toluamide); fatty acid esters (e.g., n-butyrate); organic acids (e.g., citric acid); polyols (e.g., ethylene glycol, glycerol); sulfoxides (e.g., dimethylsulfoxide); terpenes (e.g., cyclohexene); ureas; sugars; carbohydrates or other agents. In certain embodiments, the penetrating agent includes a salt, e.g., as described herein.

Thus, another aspect of the invention provides for the delivery of pharmaceutical agents (e.g., drugs, biological compounds, etc.) into the body, and such treatments may be systemic or localized, e.g., directed to a specific location of the body of a subject, such as the head, one or more specific muscles, an arm, a leg, the genitals, etc., depending on the specific application.

In one set of embodiments, pharmaceutical agents are introduced to aid in treatment of medical conditions or diseases, and the symptoms associated thereof. In some embodiments, the invention provides for the treatment of medical conditions or diseases and/or ailments using pharmaceutical agents (for example, to treat a subject diagnosed with a medical condition or disease), and in some cases, the invention provides for the delivery of a minimum amount of pharmaceutical agents to provide effective levels of medication to an effected area topically while limiting side effects. In some cases, the effective dosage of the pharmaceutical agent may be lower than the effective dosage of the pharmaceutical agent when taken orally. Other embodiments of the invention provide methods for treating pain, for example, pain from migraine, pain from arthritis, other headaches, joint pain, muscle pain and other types of pain. Accordingly, in some embodiments, a composition may be topically applied to a specific location of the body, e.g., to a site of pain. Also, in certain cases, a composition as described herein may be used in the preparation of a medicament for treatment of pain, or other diseases or conditions as discussed herein.

In another aspect, the present invention is directed to a kit including one or more of the compositions discussed herein. A "kit," as used herein, typically defines a package or an assembly including one or more of the compositions of the invention, and/or other compositions associated with the invention, for example, as described herein. Each of the compositions of the kit may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions or components associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, and the like, for example, for using, administering, modifying, assembling, storing, packaging, preparing, mixing, diluting, and/or preserving the compositions components for a particular use, for example, to a sample and/or a subject.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the compositions and/or other compositions associated with the kit. In some cases, the instructions may also include instructions for the delivery and/or administration of the compositions, for example, for a particular use, e.g., to a sample and/or a subject. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

In some embodiments, the present invention is directed to methods of promoting one or more embodiments of the invention as discussed herein, for example, methods of promoting the making or use of compositions such as those discussed above, methods of promoting kits as discussed above, or the like. As used herein, "promoted" includes all methods of doing business including, but not limited to, methods of selling, advertising, assigning, licensing, contracting, instructing, educating, researching, importing, exporting, negotiating, financing, loaning, trading, vending, reselling, distributing, repairing, replacing, insuring, suing, patenting, or the like that are associated with the systems, devices, apparatuses, articles, methods, compositions, kits, etc. of the invention as discussed herein. Methods of promotion can be performed by any party including, but not limited to, personal parties, businesses (public or private), partnerships, corporations, trusts, contractual or sub-contractual agencies, educational institutions such as colleges and universities, research institutions, hospitals or other clinical institutions, governmental agencies, etc. Promotional activities may include communications of any form (e.g., written, oral, and/or electronic communications, such as, but not limited to, e-mail, telephonic, Internet, Web-based, etc.) that are clearly associated with the invention.

In one set of embodiments, the method of promotion may involve one or more instructions. As used herein, "instructions" can define a component of instructional utility (e.g., directions, guides, warnings, labels, notes, FAQs or "frequently asked questions," etc.), and typically involve written instructions on or associated with the invention and/or with the packaging of the invention. Instructions can also include instructional communications in any form (e.g., oral, electronic, audible, digital, optical, visual, etc.), provided in any manner such that a user will clearly recognize that the instructions are to be associated with the invention, e.g., as discussed herein.

The following documents are incorporated herein by reference: International Patent Application No. PCT/US98/19429, filed Sep. 17, 1998, entitled "A Delivery of Arginine to Cause Beneficial Effects," by E. T. Fossel, published as WO 99/13717 on Mar. 25, 1999; U.S. patent application Ser. No. 11/587,323, filed Oct. 19, 2006, entitled "Transdermal Delivery of Beneficial Substances Effected by a Hostile Biophysical Environment," by E. T. Fossel, published as U.S. Patent Application Publication No. 2008/0280984 on Nov. 13, 2008; and U.S. patent application Ser. No. 11/587,328, filed Oct. 19, 2006, entitled "Beneficial Effects of Increasing Local Blood Flow," by E. T. Fossel, published as U.S. Patent Application Publication No. 2009/0105336 on Apr. 23, 2009.

Also incorporated herein by reference are International Patent Application No. PCT/US2005/005726, filed Feb. 23, 2005, entitled "Topical Delivery of a Nitric Oxide Donor to Improve Body and Skin Appearance," by E. Fossel, published as WO 2005/081964 on Sep. 9, 2005; International Patent Application No. PCT/US2005/013228, filed Apr. 19, 2005, entitled "Transdermal Delivery of Beneficial Substances Effected by a Hostile Biophysical Environment," by E. Fossel, published as WO 2005/102282 on Nov. 3, 2005; International Patent Application No. PCT/US2005/013230, filed Apr. 19, 2005, entitled "Beneficial Effects of Increasing Local Blood Flow," by E. Fossel, published as WO 2005/102307 on Nov. 3, 2005; U.S. patent application Ser. No. 08/932,227, filed Sep. 17, 1997, entitled "Topical Delivery of Arginine of Cause Beneficial Effects," by E. T. Fossel, published as 2002/0041903 on Apr. 11, 2002; U.S. patent application Ser. No. 10/201,635, filed Jul. 22, 2002, entitled "Topical Delivery of L-Arginine to Cause Beneficial Effects," by E. T. Fossel, published as 2003/0028169 on Feb. 6, 2003; U.S. patent application Ser. No. 10/213,286, filed Aug. 5, 2002, entitled "Topical and Oral Arginine to Cause Beneficial Effects," by E. T. Fossel, published as 2003/0018076 on Jan. 23, 2003; U.S. Pat. No. 5,895,658, issued Apr. 20, 1999, entitled "Topical Delivery of L-Arginine to Cause Tissue Warming," by E. T. Fossel; U.S. Pat. No. 5,922,332, issued Jul. 13, 1999, entitled "Topical Delivery of Arginine to Overcome Pain," by E. T. Fossel; U.S. Pat. No. 6,207,713, issued Mar. 27, 2001, entitled "Topical and Oral Delivery of Arginine to Cause Beneficial Effects," by E. T. Fossel; and U.S. Pat. No. 6,458,841, issued Oct. 1, 2002, entitled "Topical and Oral Delivery of Arginine to Cause Beneficial Effects," by E. T. Fossel.

In addition, incorporated herein by reference in their entireties are U.S. Provisional Patent Application Ser. No. 61/428,003, filed Dec. 29, 2010, entitled "Systems and Methods for Treatment of Allergies and Other Indications," by E. T. Fossel; and U.S. Provisional Patent Application Ser. No. 61/428,213, filed Dec. 29, 2010, entitled "Methods and Compositions for Preparing Emulsions for Topical Drug Delivery," by E. T. Fossel.

The following examples are intended to illustrate certain embodiments of the present invention, but do not exemplify the full scope of the invention.

EXAMPLE 1

This prophetic example illustrates one method of preparing a transdermal formula of the invention including fexofenadine, cetirizine, diphenhydramine, or loratadine. The final composition is shown in Table 1. Of course, those of ordinary skill in the art will understand that percentages other than the ones listed below are also possible, according to other embodiments of the invention.

TABLE 1

| Ingredient | % w/w |
|---|---|
| Water | 35-55 |
| Sodium Chloride | 2.5-15 |
| L-Arginine Hydrochloride | 2.5-15 |

TABLE 1-continued

| Ingredient | % w/w |
|---|---|
| Fexofenadine, Cetirizine, Diphenhydramine, or Loratadine | 0.1-5 |
| Glyceryl Stearate (SE) | 4-10 |
| Cetyl Alcohol | 4-10 |
| Magnesium Sulfate/Chloride | 2.5-15 |
| Squalane | 1-8 |
| Xanthan Gum | 0.2-2 |
| Isopropyl Myristate | 0.1-5 |
| Oleic Acid | 0.1-5 |
| Propylene Glycol | 1-10 |
| Polysorbate-20 | 0.1-5 |
| Vitamin E | 0.1-1 |

To prepare the formulation in this example, sodium chloride, potassium chloride, L-arginine and fexofenadine, cetirizine, diphenhydramine, or loratadine were mixed in water, then heated to 74° C. with rapid mixing. In a separate container, the remaining ingredients were mixed together and heated to 74° C. The other ingredients were then added to the water phase at 74° C. with rapid mixing. The mixture was then cooled to room temperature with continued mixing. At this point, an emulsion formed with a relatively thin consistency. The emulsion was then homogenized at high speed at room temperature to thicken the consistency.

EXAMPLE 2

Initially, it should be appreciated that the compositions described in this example for the first aqueous and second non-aqueous preparations for use with ibuprofen may be used for other drugs or other pharmaceutical agents such as those described herein (e.g., an $H_1$ antihistamine), or may be modified to contain equivalent or similar compounds (or a subset thereof) for use with different drugs or other pharmaceutical agents, and each drug or other pharmaceutical agent may individually be provided in the first preparation, the second preparation, or both.

Ibuprofen sodium salt is water soluble at pH 7.0 and is added to the water phase. Any suitable ibuprofen salt may be used. For example, a commercially available ibuprofen salt may be used. In some embodiments, an ibuprofen preparation is manufactured to have the following relative composition (Table 2).

TABLE 2

| Ingredient | Quality | % w/w |
|---|---|---|
| Water | USP | 40.9 |
| Sodium Chloride | USP | 10.0 |
| L-Arginine Hydrochloride | USP | 7.5 |
| Ibuprofen | USP | 7.5 |
| Sodium Hydroxide | USP | 1.3 |
| Glyceryl Stearate (SE) | | 7.0 |
| Cetyl Alcohol | NF | 7.0 |
| Potassium Chloride | USP | 5.0 |
| Squalane | NF | 4.0 |
| Xanthan Gum | FCC | 0.8 |
| Isopropyl Myristate | NF | 1.0 |
| Oleic Acid | NF | 1.0 |
| Propylene Glycol | USP | 5.0 |
| Polysorbate-20 | NF | 2.0 |

The basic manufacturing process is to form an emulsion by mixing a water phase and an oil phase at elevated temperature with rapid mixing. Once the two phases are mixed the mixture is cooled to room temperature. While cooling is being accomplished homomixing is accomplished with a vertical colloid mill. For example, in one set of embodiments, the following manufacturing steps can be used:

Step 1: disperse xanthan gum in the propylene glycol and water and mix to fully hydrate.

Step 2: To the above mixture add ibuprofen and sodium hydroxide to produce sodium ibuprofen, add sodium chloride, potassium chloride and 1-arginine HCl. Heat this mixture to 75° C. to 80° C.

Step 3: Add glyceryl stearate SE, cetyl alcohol, squalane, isopropyl myristate, oleic acid and polysorbate-20 and heat this mixture to 75° C. to 80° C.

Step 4: Combine the mixtures produced in Step 2 and Step 3 and mix well maintaining temperature.

Step 5: Cool the mixture of Step 4 to 25° C. to 30° C. while circulating through the vertical colloid mill.

The resulting smooth emulsion has a pH of 6.50 to 7.50. In some cases, the preparation can be manufactured under conditions to minimize microbial content (e.g., completely sterile or with a microbiological content of less than about 100 CFU/g).

In some embodiments, a transdermal ibuprofen cream is packaged in 100 ml "Magic Star Dispensers" which are airless pumps. The pump dispenses 1.45 ml with each depression of the pump head.

In some embodiments, the active compound (e.g., diphenhydramine) may be added to the aqueous phase prior to mixing with the oil phase. However, other compounds may be added to the oil phase prior to mixing with the aqueous phase.

EXAMPLE 3

Use of a Diphenhydramine Composition

A 19 year old male with a tendency to develop hives was given a cream containing 7.5% diphenhydramine in an oil/water emulsion to which 10% sodium chloride and 5% magnesium chloride was added. The pH of the cream was 7.2. The subject was at an outdoor sporting event when he developed a moderate case of hives over the exposed upper part of his body. Immediately he applied approximately 5 grams of cream and the attack began to subside with complete resolution within 20 minutes.

The formula for the topical composition that was used for diphenhydramine is provided in Table 3 below (shown as % weight). It should be appreciated that the relative amounts of each component may be varied (e.g., by about 10%) in some embodiments. It also should be appreciated that this topical composition may be used for other antihistamines (e.g., one or more examples of $H_1$ antihistamines including, but not limited to, fexofenadine, cetirizine (or levocertrizine), clemastine, diphenhydramine, doxylamine, pheniramine, ebastine, chlorpheniramine, meclizine, embramine, dexchlorpheniramine, and loratadine).

In some embodiments, the active compound may be added to the oil phase prior to mixing with the aqueous phase. However, other compounds (e.g., diphenhydramine) may be added to the aqueous phase prior to mixing with the oil phase.

TABLE 3

| Ingredient | % |
|---|---|
| purified water | 41 |
| propylene glycol | 5 |
| xanthum gum | 0.8 |
| active ingredient | 7.5 |
| sodium chloride | 10 |

TABLE 3-continued

| Ingredient | % |
|---|---|
| potassium chloride | 0 |
| magnesium chloride | 5 |
| L-Arginine HCl | 7.5 |
| Glyceryl Stearate SE | 6.5 |
| Cetyl Alcohol | 6.5 |
| Squalane | 3.5 |
| Isopropyl Myrstate | 2 |
| Oleic Acid | 2 |
| Polysorbate 20 | 2 |

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition for topical delivery to the skin of a subject, the composition comprising:
    an ionic salt;
    a stabilization polymer comprising xanthan gum;
    propylene glycol;
    a polysorbate surfactant comprising polysorbate 20;
    an $H_1$ antihistamine and/or a salt thereof; and
    a nitric oxide donor comprising L-arginine and/or L-arginine hydrochloride.
2. The composition of claim 1, wherein the composition is stable when exposed to a temperature of 40° C. for at least about 4 weeks.
3. The composition of claim 1, wherein the composition is a cream.
4. The composition of claim 1, wherein the composition is contained within a transdermal patch.
5. The composition of claim 1, wherein the nitric oxide donor is present at a concentration of at least about 0.5% by weight of the composition.
6. The composition of claim 1, wherein the composition is capable of driving the $H_1$ antihistamine and/or salt thereof through stratum corneum.
7. The composition of claim 1, wherein the ionic salt is present at a concentration of at least about 5% by weight of the composition.
8. The composition of claim 1, wherein the ionic salt comprises one or more salts selected from the group consisting of sodium chloride, choline chloride, magnesium chloride, and calcium chloride.
9. The composition of claim 1, wherein the composition has an ionic strength of at least about 0.25 M.
10. The composition of claim 1, wherein the composition has an ionic strength of at least about 1 M.
11. The composition of claim 1, wherein the composition has a pH of at least about 7.
12. The composition of claim 1, wherein the composition further comprises a package containing the nitric oxide donor, the package being selected from the group consisting of liposomes, emulsions of collagen, collagen peptides and combinations thereof.
13. The composition of claim 1, wherein the stabilization polymer is present at a concentration of at least about 0.5% by weight of the composition.
14. The composition of claim 1, wherein the propylene glycol is present at a concentration of at least about 1% by weight of the composition.
15. The composition of claim 1, wherein the polysorbate surfactant is present at a concentration of at least about 1% by weight of the composition.
16. The composition of claim 1, wherein the $H_1$ antihistamine is fexofenadine.
17. The composition of claim 1, wherein the $H_1$ antihistamine is cetrizine.
18. The composition of claim 1, wherein the $H_1$ antihistamine is clemastine.
19. The composition of claim 1, wherein the $H_1$ antihistamine is diphenhydramine.
20. The composition of claim 1, wherein the $H_1$ antihistamine is doxylamine.
21. The composition of claim 1, wherein the $H_1$ antihistamine is pheniramine.
22. The composition of claim 1, wherein the $H_1$ antihistamine is ebastine.
23. The composition of claim 1, wherein the $H_1$ antihistamine is chlorpheniramine.
24. The composition of claim 1, wherein the $H_1$ antihistamine is meclizine.
25. The composition of claim 1, wherein the $H_1$ antihistamine is embramine.
26. The composition of claim 1, wherein the $H_1$ antihistamine is dexchlorpheniramine.
27. The composition of claim 1, wherein the $H_1$ antihistamine is loratadine.
28. The composition of claim 1, wherein the $H_1$ antihistamine and/or salt thereof is present at a concentration of at least about 0.1% by weight of the composition.
29. The composition of claim 1, wherein the composition further comprises an antioxidant.
30. The composition of claim 29, wherein the antioxidant comprises vitamin E.
31. A method, comprising applying the composition of claim 1 to a subject.

32. A composition for topical delivery to the skin of a subject, wherein at least about 80% by weight of the composition comprises:
  water;
  at least one chloride salt;
  a stabilization polymer comprising xanthan gum;
  propylene glycol;
  a polysorbate surfactant comprising polysorbate 20;
  an $H_1$ antihistamine and/or a salt thereof; and
  a nitric oxide donor.

33. The composition of claim 32, wherein the composition has a pH of at least about 7.

34. The composition of claim 32, wherein the composition further comprises an antioxidant.

35. The composition of claim 34, wherein the antioxidant comprises vitamin E.

36. The composition of claim 34, wherein the antioxidant is present at a concentration of between about 0.1% and about 1% by weight of the composition.

37. The composition of claim 32, wherein the composition further comprises glyceryl stearate.

38. The composition of claim 32, wherein the composition further comprises cetyl alcohol.

39. The composition of claim 32, wherein the composition further comprises squalane.

40. The composition of claim 32, wherein the composition further comprises isopropyl myristate.

41. The composition of claim 32, wherein the composition further comprises oleic acid.

42. The composition of claim 32, wherein the water is present at a concentration of at least about 35% by weight of the composition.

43. The composition of claim 32, wherein the water is present at a concentration of at least about 40% by weight of the composition.

44. A composition for topical delivery to the skin of a subject, the composition consisting essentially of:
  water;
  sodium chloride;
  glyceryl stearate;
  cetyl alcohol;
  magnesium sulfate and/or magnesium chloride;
  squalane;
  a stabilization polymer comprising xanthan gum;
  isopropyl myristate;
  oleic acid;
  propylene glycol;
  a polysorbate surfactant comprising polysorbate 20;
  an antioxidant;
  an $H_1$ antihistamine and/or a salt thereof; and
  a nitric oxide donor.

45. A composition for topical delivery to the skin of a subject, the composition comprising each of the following compounds at concentrations of no more than ±20% of the stated concentrations:
  water at a concentration of about 35% to about 55% by weight;
  sodium chloride at a concentration of about 2.5% to about 15% by weight;
  glyceryl stearate at a concentration of about 4% to about 10% by weight;
  magnesium chloride at a concentration of about 2.5% to about 15% by weight;
  squalane at a concentration of about 1% to about 8% by weight;
  a polysorbate surfactant comprising polysorbate 20 at a concentration of about 0.2% to about 2% by weight;
  isopropyl myristate at a concentration of about 0.1% to about 5% by weight;
  oleic acid at a concentration of about 0.1% to about 5% by weight;
  propylene glycol at a concentration of about 1% to about 10% by weight;
  a stabilization polymer comprising xanthan gum at a concentration of about 1% to about 10% by weight;
  an antioxidant at a concentration of about 0.1 to about 1% by weight;
  an $H_1$ antihistamine and/or a salt thereof at a concentration of about 0.1% to about 5% by weight; and
  a nitric oxide donor at a concentration of about 2.5% to about 15% by weight.

\* \* \* \* \*

UNITED STATES PATENT AND TRADEMARK OFFICE
CERTIFICATE OF CORRECTION

PATENT NO.        : 9,289,495 B2  
APPLICATION NO.   : 13/977511  
DATED             : March 22, 2016  
INVENTOR(S)       : Eric T. Fossel Page 1 of 1

It is certified that error appears in the above-identified patent and that said Letters Patent is hereby corrected as shown below:

On the title page, Item (60) should read:

(60)  Provisional application No. 61/428,003, filed on Dec. 29, 2010, provisional application No. 61/428,213, filed on Dec. 29, 2010.

Signed and Sealed this  
Twenty-fourth Day of May, 2016

Michelle K. Lee  
*Director of the United States Patent and Trademark Office*